United States Patent
Cohee et al.

(10) Patent No.: US 7,431,837 B2
(45) Date of Patent: Oct. 7, 2008

(54) MIXING VESSEL AND METHOD OF USE

(75) Inventors: Donald R. Cohee, Felton, DE (US); Ajay K. Prasad, Newark, DE (US)

(73) Assignee: ILC Dover LP, Frederica, DE (US)

(*) Notice: Subject to any disclaimer, the term of this patent is extended or adjusted under 35 U.S.C. 154(b) by 72 days.

(21) Appl. No.: 11/406,496

(22) Filed: Apr. 19, 2006

(65) Prior Publication Data

US 2006/0254983 A1    Nov. 16, 2006

Related U.S. Application Data

(63) Continuation-in-part of application No. 10/777,088, filed on Feb. 13, 2004, now Pat. No. 7,033,499.

(60) Provisional application No. 60/447,011, filed on Feb. 13, 2003.

(51) Int. Cl.
*B01D 63/00* (2006.01)
*B01L 11/00* (2006.01)
*B02C 11/08* (2006.01)

(52) U.S. Cl. .............. 210/321.75; 210/416.1; 210/499; 210/175; 422/101; 100/38; 100/116; 100/349; 100/316

(58) Field of Classification Search ............ 210/321.75, 210/416.1, 488, 472, 321.68, 321.84, 261, 210/768, 175, 7, 767; 604/4, 5, 408; 422/99, 422/101; 424/472; 524/221; 100/38, 116, 100/369, 316

See application file for complete search history.

(56) References Cited

U.S. PATENT DOCUMENTS

| | | | |
|---|---|---|---|
| 2,962,201 A | 11/1960 | Brillis | |
| 3,190,619 A | 6/1965 | Penney | |
| 4,114,522 A | 9/1978 | Nagamine | |
| 4,177,575 A | 12/1979 | Brooks | |
| 4,242,001 A | 12/1980 | Meintker | |
| 4,436,458 A | 3/1984 | Wisdom | |
| 4,548,509 A | 10/1985 | Parrott | |
| 4,560,382 A | 12/1985 | Isono | |
| 4,859,336 A * | 8/1989 | Savas et al. ............... | 210/416.1 |
| 4,952,068 A | 8/1990 | Flint | |
| 4,966,468 A | 10/1990 | Bruning | |

(Continued)

FOREIGN PATENT DOCUMENTS

DE    3838530    5/1990

(Continued)

OTHER PUBLICATIONS

Supplemental European Search Report issued Apr. 26, 2006.

*Primary Examiner*—Ana M Fortuna
(74) *Attorney, Agent, or Firm*—Novak Druce & Quigg LLP

(57) ABSTRACT

A mixing vessel contains a septum, dividing a first chamber from a second chamber. By relatively moving the septum with respect to the ends of the vessel, and flowing a fluid through the septum, the fluid is treated as it moves from the first chamber to the second chamber. The particular configuration of the septum allows for treatments such as mixing, reacting, heating, and cooling, as well as filtering of the fluid.

22 Claims, 17 Drawing Sheets

U.S. PATENT DOCUMENTS

| | | | |
|---|---|---|---|
| 4,981,596 A | | 1/1991 | Shiino |
| 5,079,170 A | * | 1/1992 | Rosman et al. ............. 436/178 |
| 5,328,464 A | | 7/1994 | Kriesel |
| 5,350,513 A | | 9/1994 | Markowitz |
| 5,364,539 A | * | 11/1994 | Castagno et al. ............ 210/768 |
| 5,555,796 A | | 9/1996 | Kortschot |
| 5,658,463 A | * | 8/1997 | Rubio ........................ 210/634 |
| 5,685,980 A | * | 11/1997 | Patapoff et al. ............. 210/244 |
| 5,772,644 A | | 6/1998 | Bark |
| 5,795,330 A | | 8/1998 | Tofighi |
| 5,868,495 A | | 2/1999 | Hidalgo |
| 5,941,635 A | | 8/1999 | Stewart |
| 5,955,032 A | * | 9/1999 | Kelly et al. ................. 422/100 |
| 6,029,563 A | | 2/2000 | Nakagawa |
| 6,076,457 A | | 6/2000 | Vallot |
| 6,089,143 A | | 7/2000 | Figueroa |
| 6,189,704 B1 | | 2/2001 | Dennehey |
| 6,190,913 B1 | | 2/2001 | Singh |
| 6,213,007 B1 | | 4/2001 | Lande |
| 6,221,264 B1 | | 4/2001 | Ishida |
| 6,251,291 B1 | | 6/2001 | Lamphere |
| 6,279,463 B1 | | 8/2001 | Kajiwara |
| 6,364,520 B1 | | 4/2002 | Steele |
| 6,416,215 B1 | | 7/2002 | Terentiev |
| 6,447,158 B1 | | 9/2002 | Farkas |
| 6,497,823 B1 | | 12/2002 | Rothman |
| 6,544,788 B2 | | 4/2003 | Singh |
| 6,653,377 B1 | * | 11/2003 | Lloyd et al. ................. 524/221 |
| 6,682,565 B1 | | 1/2004 | Rothman |
| 6,821,790 B2 | | 11/2004 | Mahant |
| 7,033,499 B2 | * | 4/2006 | Cohee et al. ........... 210/321.75 |

FOREIGN PATENT DOCUMENTS

| | | |
|---|---|---|
| EP | 0674888 | 10/1995 |
| GB | 1173509 | 12/1969 |
| JP | 55092130 | 7/1980 |

* cited by examiner

FIG. 4
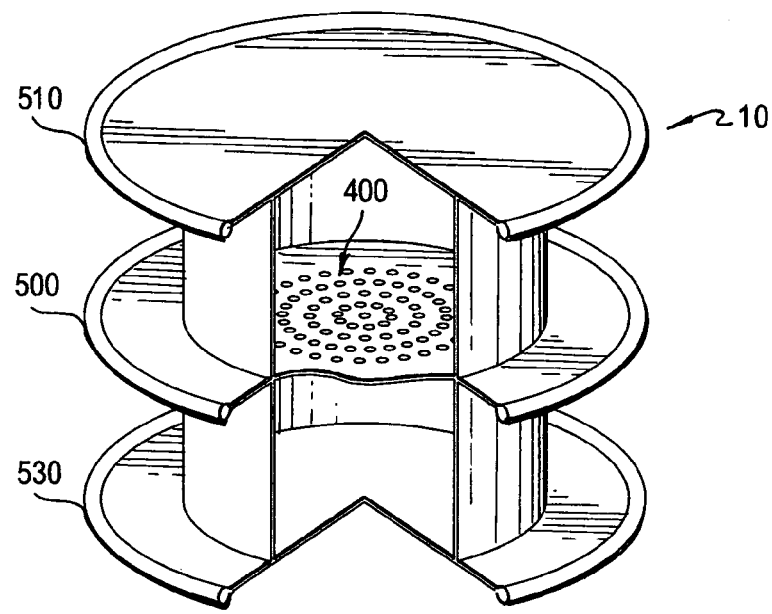
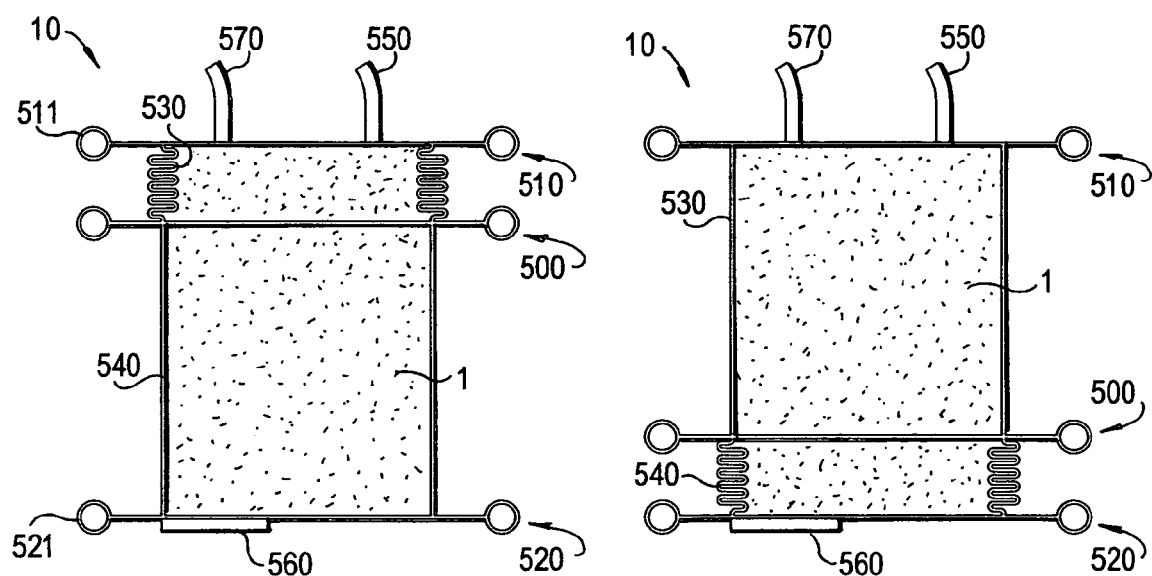
FIG. 6A          FIG. 6B

US 7,431,837 B2

MIXING VESSEL AND METHOD OF USE

CROSS-REFERENCE TO RELATED APPLICATIONS

This application is a Continuation-in-Part of U.S. application Ser. No. 10/777,088, filed Feb. 13, 2004, and claims domestic priority of provisional application Ser. No. 60/447,011, filed Feb. 13, 2003, the entire disclosures of which are herein incorporated by reference in their entireties.

BACKGROUND OF THE INVENTION

1. Field of the Invention

In one embodiment, the invention relates to a flexible, sterile, sealable or sealed and at least partially or completely disposable vessel for performing any or all of mixing, heating, cooling, filtering, separating, forming cakes, drying, fermenting, blending powders, reacting chemicals and storing, which can be done with or without a gaseous head. Such vessels may be used (or, in some cases, re-used) as (1) a storage container optionally with heating/cooling with the optional application of mixing; or (2) a small flexible mixer that can be actuated by hand, in mechanical situations as needed, such as in mixing paint. In other embodiments, the invention relates to apparatus and method for mixing and/or dispensing pigments/dyestuffs into highly viscous materials.

2. Description of the Related Art

Improving processes to make various chemical compounds, such as powder, is a major focus of the pharmaceutical industry. With the rising costs of the drugs and other products or chemicals, manufacturers of such items have looked to innovation and mass production to reduce the manufacturing costs and streamline processes. However, there continues to be the costs and attendant disadvantages of maintaining "clean rooms" so as to prevent the introduction of contaminants into the process as well as the need to protect workers with at least one of protective masks, suits, or other protection equipment because of the potential risk of exposure to the reactants and/or products of such processes. Additionally, cleaning and certification or validation of equipment and piping tends to greatly increase costs.

In addition, conventional chemical processing has used separate equipment to perform a single function, e.g., a mixing vessel is distinct from a reactor or filter. However, by the disclosed invention, it is possible to perform multiple unit operations of chemical processes in a single vessel.

Conventional manufacturing, mixing and/or stirring systems have been used in this type of industry for a considerable period of time. In a typical pharmaceutical powder production system for example, the various ingredients or components are introduced into an array of rigid vessels each of which perform some single function. FIG. 1 illustrates a typical process. Chemicals or components are introduced into a mixer 110 where they are mixed by a known method, e.g., a stirrer. The mixture is then transferred into one or more reactors 120, which causes a reaction of the components by heat, pressure, etc. and other components may be added as well. Following the reaction, the material is again transferred to a centrifuge 130 for separation of undesired material. Finally, the material is dried in a dryer 140 to remove liquid components and form the desired powder, which is again transferred to a storage location 150.

Another and more complicated system for a typical biopharmaceutical process is illustrated in FIG. 2. It generally has a similar step-by-step process as the process outlined above, but with more separated locations to perform certain processes. For example, the system has a pair of media mixers 200, a pair of fermenters 210, several filtration vessels 230, which may be microfiltration vessels, ultrafiltration vessels, sterile filtration vessels, etc., dialfiltration buffer vessels 240, and chromatography buffer vessels 250. Additionally, each of the vessels has at least a pair of ports for addition of other material as well as removal of waste material. The whole system yields a multitude of vessels for the production of a single desired material.

Other problems associated with these processes is with the multitude of vessels and transference means is the likelihood of leaks in the system, undesired material entering the system, material from a previous process remaining in the vessel which interferes with a subsequent process, etc.

When a large scale production is required, the glass beaker of laboratory scale may be replaced by a large metal vat or other conventional industrial vessel that also provides heating and cooling capacity. In either system, the components are sequentially or consecutively added to the vessel where the mixing and/or stirring is conducted. In such systems, a stirring device is generally inserted through the upper, open face of the container and powered from an external source. Additionally, reuse of the conventional system requires significant cleaning and sterilization processes to ensure the absence of undesirable materials. The associated costs of cleaning/sterilization and recertification of the equipment prior to reuse is a major disadvantage of the prior art avoided by the present inention.

Furthermore, the traditional beaker of the laboratory or the industrial vat mixing systems require intervention between the beaker and the mixing means, which can also introduce contaminants and render the process less efficient. Examples include those described in U.S. Pat. No. 5,941,635 and No. 4,114,522, each of which is herein incorporated by reference in its entirety.

Other designs require sophisticated manipulation of the vessel to mix the material contained therein by rocking the vessel about an axis, such as those disclosed in U.S. Pat. No. 6,190,913. Still further designs require the user to mix the material by squeezing a flexible vessel, such as that disclosed in U.S. Pat. No. 5,795,330. Other designs use passing a fluid through a mixing disk, such as those shown in U.S. Pat. Nos. 5,868,495 and 6,447,158. Finally, others oscillate the mixing disk through the fluid, such as those shown in U.S. Pat. Nos. 4,966,468 and 4,436,458. However, such mixing apparatus are rigid structures and do not effectively reduce the multitude of vessels require to perform a single process.

As a result of the streamlining of the process to make materials, the biopharmaceutical process industry needs technologies that use disposable manufacturing components versus stainless steel tanks and piping. An example of such a vessel is disclosed in the co-pending application U.S. Ser. No. 10/256,070 filed Sep. 27, 2002, which is assigned to the present assignee and is herein incorporated by reference in its entirety. However, such methods and apparatus disclosed therein require the use of several disposable vessels for the production of a typical material.

SUMMARY OF THE INVENTION

An object of the invention is to overcome the problems outlined above using traditional vessels in production of pharmaceutical materials, biopharmaceutical materials, chemicals, chemical formulations, and other various materials. Another object of invention is to reduce the number of vessels needed in such a production process. A further object is to reduce the likelihood of entrance of contaminants into the vessels during the production process. A still further object is to eliminate the costs associated with cleaning, sterilization and revalidation of a vessels and piping used in the foregoing industries.

These problems as well as others are overcome using a mechanically actuated flexible containment vessel that is configured to perform various manufacturing processes. The vessel comprises a high strength flexible polymer or coated fabric with low extractables, chemical compatibility and may operate over a broad operating/storage temperature range. The vessel should have a very low bio-burden, i.e., not support biogrowth and be sterilizable and preferably disposable by incineration. Exemplary materials are the olefins, especially polyethylene, and fluorocarbon polymers, such as PTFE. In one embodiment, the vessel has a generally two-tiered design with an upper and lower chamber and an upper and lower disk at either end and one center septum dividing the vessel into two portions creating the chambers. At an appropriate filling of the vessel with materials to be processed, e.g., full half of a chamber to allow run length for moving the center septum, the center septum relatively moves between a position adjacent to the upper disk and a position adjacent to the lower disk. The center septum also has a series of holes to allow the material to pass from the upper chamber to the lower chamber. A back and forth movement of the center septum relative to the contents of the vessel forces the material to pass through the septum which stirs the material contained therein. Sterility of the contents is maintained via the use of sterile entry and exit ports on the device. Alternatively, components to be manipulated may be prepackaged in repturable bags or other frangible containers during manufacture of the vessel. In use, the component container is ruptured or otherwise opened to release the contents thereof. In another embodiment, the septum contains a, e.g., frangible membrane. Rupture of the frangible membrane, through a physical manipulation, heat, chemical or other means, allows the fluid(s) contained in the vessel to contact the active portions of the septum. Prior to rupturing of the membrane, the fluid or fluids are maintained separately, as the membrane prevents interaction with both the septum and the other fluid. Additionally, although the location of the septum has been described as being in the "center," it should be understood that any location between the interior upper and lower surfaces is sufficient.

In another embodiment, the septum is provided with a series of flutes therein that allows for hot or cold fluid to pass. As the septum is oscillated in the vessel, the temperature of the fluid passing through the septum is transferred to the material in the vessel to heat or cool the material as desired.

In a further embodiment, the center septum is provided with a series of passageways that terminate inside the vessel to allow addition of chemicals or other materials. For example, the vessel can be used as a fermentation vessel where make-up solutions are added to the material in the vessel followed by the addition of lysing solutions. The material can be left to ferment in the vessel and additionally left in the vessel for storage.

In a still further embodiment, the vessel is used as a reactor whereby the upper and lower septums are pressed together with a certain pressure by a pair of reactor plates or a pressurization system. The pressure created in the material within the vessel aids in reacting the materials therein. The center septum may also be provided with heated or cooled fluid to change the temperature of the material and may also continue mixing oscillations.

In an additional embodiment, the vessel may be used as a cross flow filtration apparatus, whereby the surface of the center septum located within the vessel is provided with a microporous coating having a vacuum source therein. Upon a mixing oscillation of the center septum, turbulent conditions are created within the vessel allowing the coating, in conjunction with the suction force or pressure, to filter out a desired particulate.

Additionally, the vessel may be used as a microfiltration vessel whereby an additional center septum is introduced into the chambers having a micro-filter. Following a mixing, heating, reacting of the material in the vessel, the material is passed through the micro-filter to remove a desired particulate or other material.

In a still further embodiment, the vessel according to the invention may be used to express a slurry into a cake. A cake fabric filter is introduced into the upper chamber of the vessel followed by an addition of slurry into the upper chamber. Through a series of manipulations of the center septum and lower disk and a filtering of liquid discharge through the cake filter and up through a vessel discharge line, the slurry is reduced to a cake. A similar process may be used to clean the cake.

In an additional embodiment, the vessel may be used to dry the cake following the above process or undry cake may be introduced into the vessel. In this embodiment, a microwave heater is placed on or under a reactor plate on the bottom of the vessel and a vent line is provided on an upper surface of the vessel exiting the chambers. Further, either the center septum has a wire grid design or an additional center septum is provided with such a wire grid design. The grid breaks up the cake material with movement of the septum and the heater dries the cake. The moisture and gas are removed from the vent line to dry the cake.

To remove the material from the vessel, a discharge chute is provided on a bottom surface thereof whereby the material may be drained or squeezed out of the vessel by kneading the vessel walls or collapsing the vessel. A bag out sleeve may be provided for the purpose of capturing vessel contents at a discrete time during the process for purposes of sampling or certifying the contents of the vessel. For example, in a process where the reaction is time dependent, a portion of the reactants/products can be expressed into the bag out sleeve, the sleeve sealed behind the sample, e.g., heat sealed and the sample analyzed to determine the progress of the reaction. The bag out sleeve may, thus, be used to capture a number of samples at different times without exposing the contents of the vessel to the outside environment or workers.

When highly viscous fluids, such as heavy oils, waxes, polymers and products such as lipstick formulations, are contained in the device of the invention, the increased viscosity makes it difficult to pass the fluid through the septum in order to, for example, to disperse a dyestuff and/or pigment therein. Instead of having the size and/or shape of the container change in order to pass fluid through the septum, it is additionally possible to have the septum move through the fluid, by being movably mounted inside a, typically rigid, container. This can be accomplished by having opposite ends of a cylindrical vessel be pistons, which causes the fluid to pass through a fixed septum as the pistons move. The use of this type of apparatus has shown the ability to satisfactorily disperse pigments and/or dyestuffs through highly viscous materials in a matter of minutes.

The vessel may have other designs and structures that use the multiple chambered vessel design as outlined above and have the above-described characteristics. For example, the vessel may be cylindrical shaped, cubic, polygonal such as square, triangular, pentagonal, hexagonal, etc.; rectangular, conical, trapezoidal, accordion style, angularly collapsible, and other shapes that are capable of providing the features outlined above.

BRIEF DESCRIPTION OF THE DRAWINGS

The embodiments, features and advantages of the invention described herein will occur to those skilled in the art from the following description of a preferred embodiment and the accompanying drawings, in which:

FIG. 4 illustrates a cut-away view of the vessel shown in FIG. 3 showing the inner chambers;

FIGS. 6A-6B illustrate a cut-away view of the vessel showing a mixing motion;

DETAILED DESCRIPTION OF THE INVENTION

Figure 1:
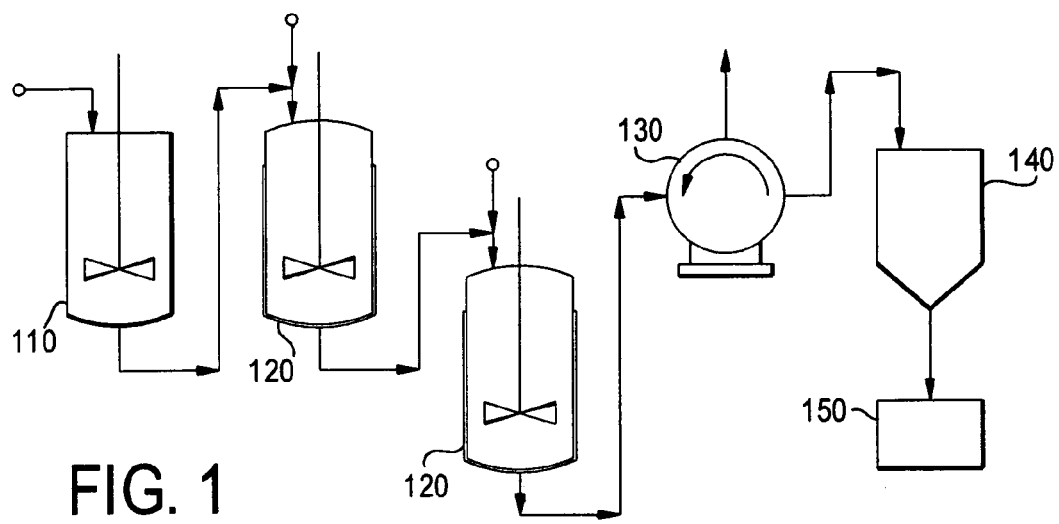
FIG. 1 is a diagram of a conventional pharmaceutical powder production process.
Figure 3:
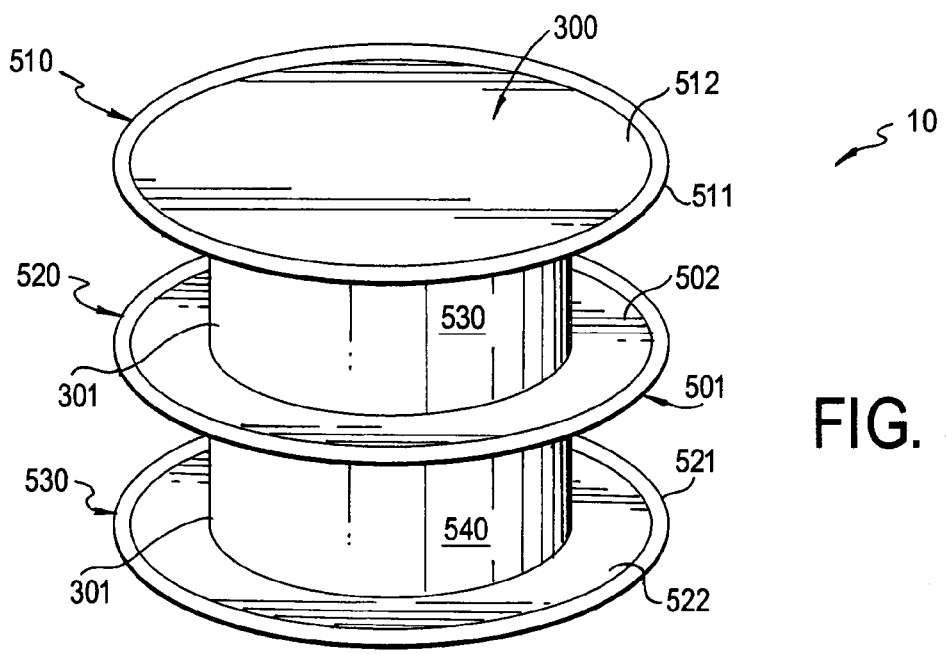
FIG. 3 illustrates a vessel according to a preferred embodiment of the present invention.

The principle embodiment of the invention is shown in FIGS. 3-6. In FIG. 3, a general design of a vessel 10 is shown. It has a generally cylindrical shape and preferably made of a high strength flexible coated fabric. Although certainly not required in every embodiment of the invention, in some applications it is possible that the vessel be transparent to permit photo initiation, or observation, e.g., highly viscous materials. In any event, it is preferred that the material be reinforced, e.g., a film reinforced by a fabric. It has an upper disk 510 and a lower disk 520 that form the upper and lower planes of the cylindrical shape. Vessel 10 also has a septum 500 subdividing the cylinder and parallel to upper and lower disks 510 and 520 thereby dividing the vessel into two portions, an upper portion and a lower portion, having side walls 530 and 540, respectively. The portions may be of equal or different volumes. The disks and the vessel walls are integrated at corners 301 via either an adhesive, overlapping of material, thermally or sonic welding, or the material from each section is integrated into the adjacent section (molding) to provide strong joints at the corners to prevent tearing and provide a strong seal. The volume of the vessel can easily be scaled up from laboratory to pilot plant to commercial processing and sizes of up to 20,000 liters and more are feasible.

Figure 7A:
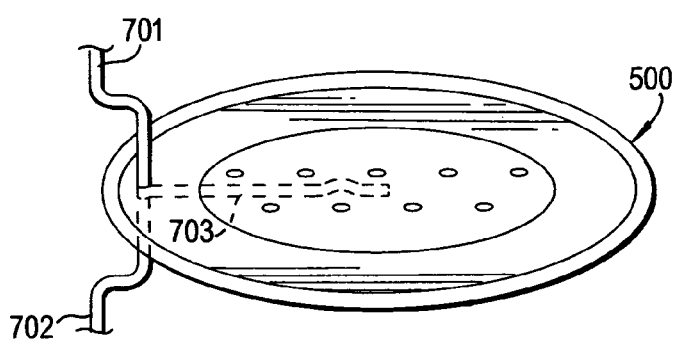
FIG. 7A illustrates another embodiment of the septum having a heating system therein.
Figure 7B:
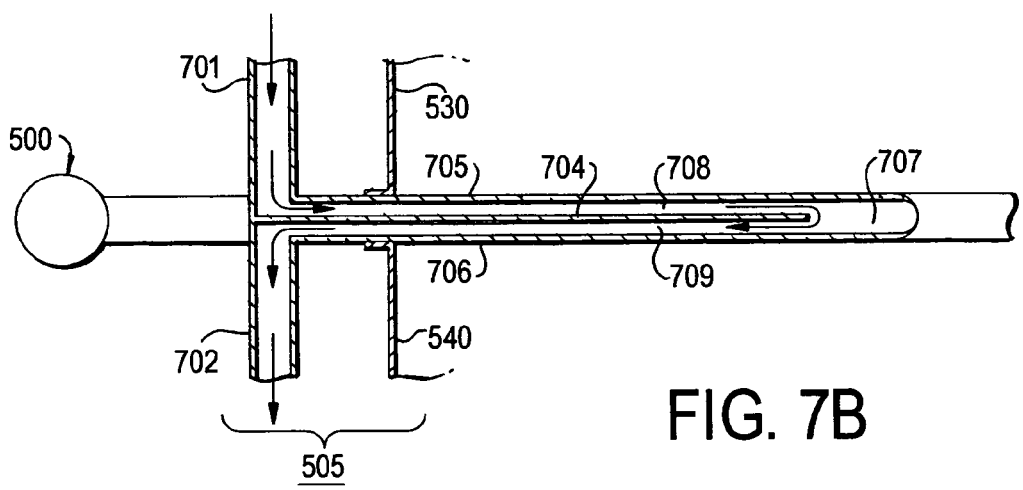
FIG. 7B illustrates a cross sectional view of the septum shown in FIG. 7A along line 7A-7A.
Figure 7C:
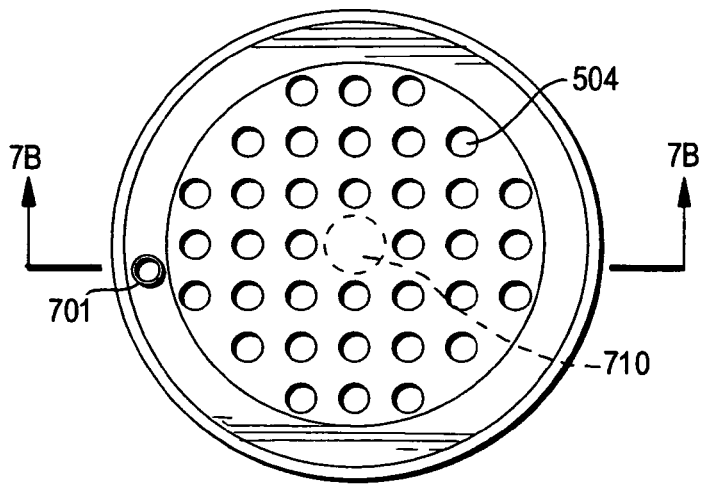
FIG. 7C illustrates another embodiment of the heating system in the septum.
Figure 7D:
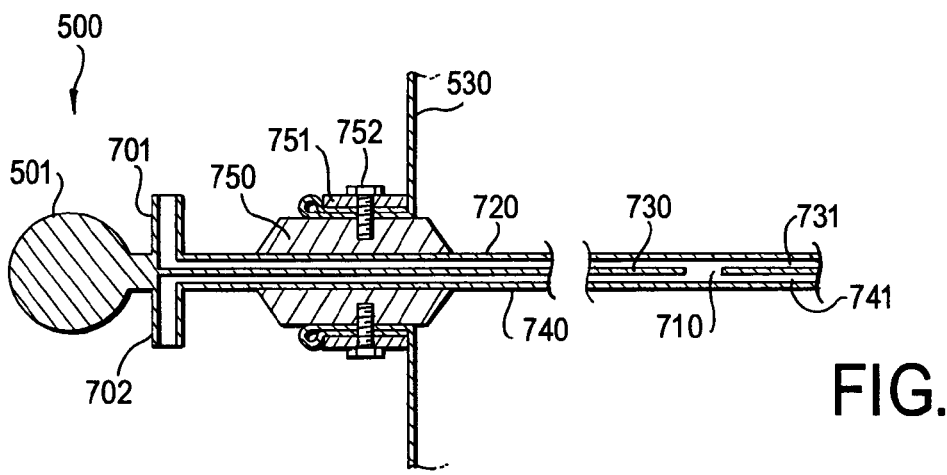
FIG. 7D illustrates a cross sectional view of the septum shown in FIG. 7C along line 7B-7B.

The disks and vessel walls may also be integrated via a clamping system, as shown in FIG. 7D, which discloses a hybrid vessel 10, whereby some or all of the septums and disks are rigid. An example is a rigid heating/cooling septum 500, described below. As shown, septum 500 is provided with a clamp base 750 integrated thereon. Clamp base 750 has a clamp ring 751 and a clamp bolt 752 mounted thereon. A portion of upper wall 530 is pulled between clamp ring 751 and clamp base 750. Clamp bolt 752 is tightened to secure the material of side wall 530 therein. The clamping system provides a solid clamp the full circumference of septum 500 to effectively secure side wall 530 to septum 500, and provide a clamp sufficient to prevent material or other fluids from entering or exiting vessel 10. Similar clamping systems may be used for upper and lower disk 510 and 520 as well.

Upper and lower disks 510 and 520 and the septum 500 have generally a planar design. Each has an outer ring, 511, 521 and 501, respectively which is generally a bead around the surface of the disk. These outer rings can be made of fabric, plastic, metal or other material and can be either stiff or flexible. They can be used for gripping vessel 10 or for securing a particular disk. Across the center of each disk inside its outer ring are flexible fabric material layers 512, 502 and 522. The flexible fabric may comprise the entire disk center or the disk may have a rigid core, made out of a plastic or metal surrounded by such material. The disks may also be made solely of the metal or plastic to create a rigid disk. For purposes of this description, the flexible fabric disks are described.

The fabric of each vessel and the disks is formed of a chemically compatible fabric with low extractables and has a broad temperature operating range. The fabric must have a sufficient material strength to be used in pressure applications. For high temperature applications, the fabric is preferably coated with PTFE (polytetrafluoroethylene) and for lower temperatures, the fabric is preferably coated with polyolefins. Such coatings in combination with the fabric material allow for the vessel to be flexible while at the same time holding various chemicals under heated, cold and/or pressure situations. While specific materials are outlined herein, other materials may be used which exhibit similar properties. It is advantageous if the materials which comprise the vessel are disposable via incineration, although in some circumstances, especially where the septum is made of metal, cast or machined to provide conduits therein that the septum is reuseable.

Figure 16:
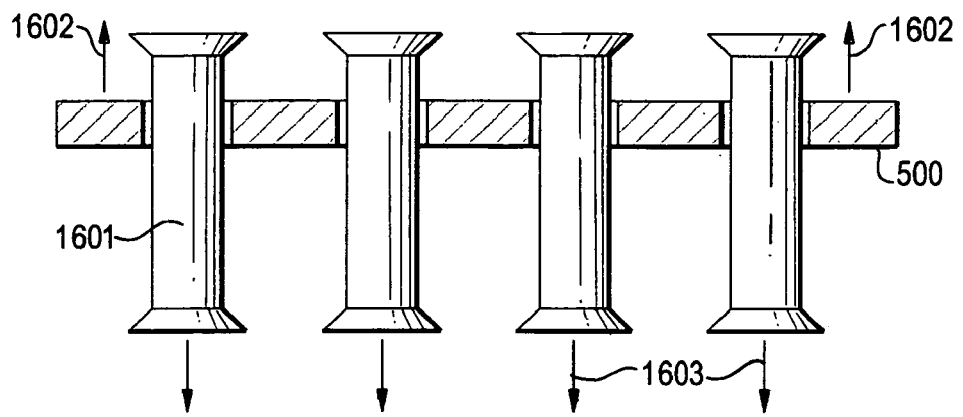
FIG. 16 illustrates a modification of the system to include flexible, thin walled tubes with flared ends mounted in the holes of the septum for relative movement therethrough.

In FIG. 4, the inner chambers of a mixing vessel 10 are shown, namely an upper chamber 11 and a lower chamber 12. Dividing the chambers is septum 500, which has a perforations region 400. When vessel 10 is filled up to a certain level (typically approximately ½ full) and the gas (or at least most of it) is expelled. Perforations 400 allow for the material to pass between the upper and lower chambers 11, 12. The open area of the perforations, expressed as a percentage of the total area of the septum, can vary, but is typically between e.g., approximately 10 and 90% or 30 and 75%, more typically between 40 and 60%, and preferably between 45 and 50%, such as 45%. Of course, it should be understood that the preferred open percentage depends upon various parameters, such as the viscosity of the materials and the sensitivity of the material to be treated. It is within the scope of the invention to modify such open area by changing the size and shape of the perforations, so as to vary the open area to an amount greater or lesser than the preferable range. In addition, as shown in FIG. 16, flexible thin walled tubes 1601 with flared ends can be inserted into the perforations of septum 500 during preassembly of the septum and can move up and down relative to the septum 500. The tubes 1601 can be made of flexible material to allow easy insertion into the perforations of septum 500 by simply bending the flared ends and forcing them into the holes. By making the tubes of slightly smaller diameter than the holes in septum 500 free movement of tubes 1601 is permitted relative to septum 500. The provision of such tubes 1601 permits travel of the tubes down through the holes in septum 500 during an upstroke in the direction of arrows 1602 of the septum 500 to expose solute to the jets 1603 for a longer duration for more efficient erosion and scouring of the bottom of vessel 10. This is particularly effective where a precipitate or solid component is present on the bottom of vessel 10.

Figure 17:
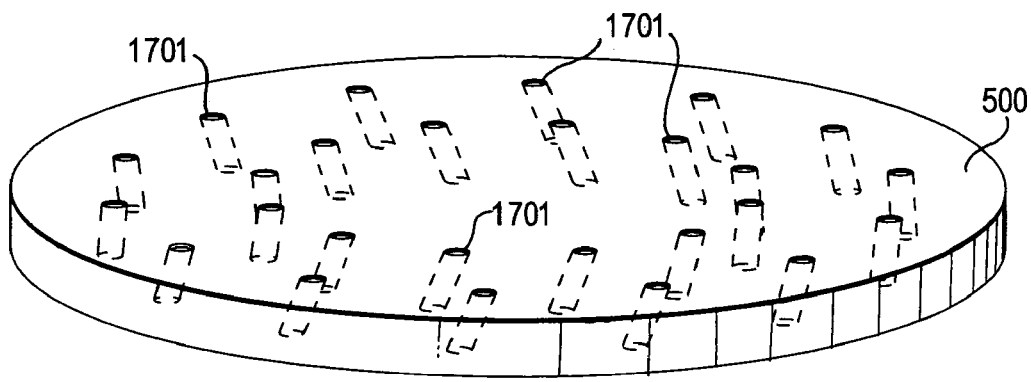
FIG. 17 shows a further modification of the septum to have the holes therethrough positioned at angles other than 90° through the septum so as to induce swirling motions.
Figure 18:
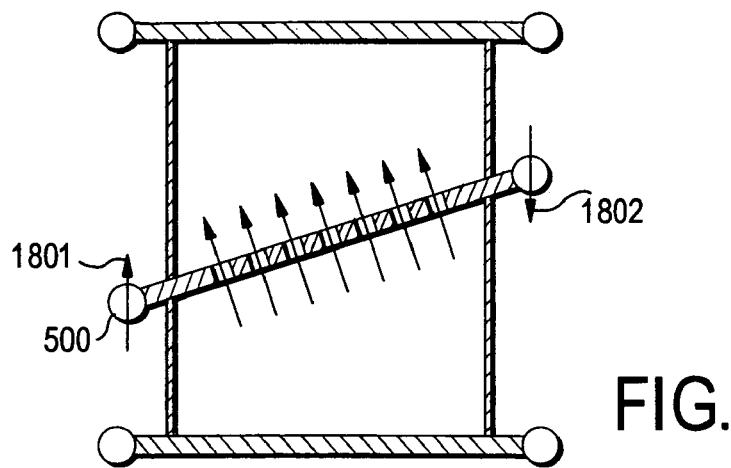
FIG. 18 shows a further modification of the septum/vessel design such that the septum does not have a strictly up and down motion with regard to the contents of the vessel but, rather, a tilting motion.

Alternative designs to cause swirling is shown in FIGS. 17, 18 and 19. As shown in FIG. 17, septum 500 is provided with perforations 1701 which are angled at other than 90° with regard to septum 500. The motion of the septum will force the fluid through the perforations 1701 at an angle such that a swirl is automatically introduced in the top chamber during a down stroke of the septum 500 and in the bottom chamber during an upstroke. The presence of swirl greatly enhances dispersion and the opportunity to increase reactivity of reactants, solvent, etc. in the vessel 10. FIG. 18 shows an alternative manner of inducing swirl by tilting septum 500 from forces 1801, 1802 applied to the opposite ends of septum 500. During tilting, a sloshing mixture is imparted to the contents of the vessel due to controlled periodic tilting. The periodic tilting motion can be performed by simply forcing two activators of the septum 500 to oscillate at a 45° to 90° out of phase arrangement.

Figure 19A:
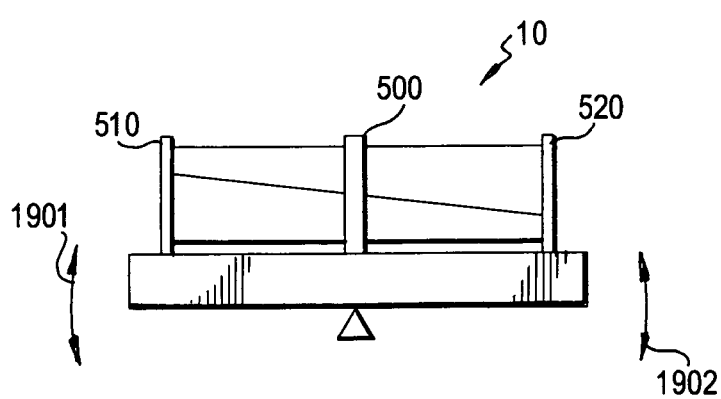
FIG. 19A shows a further modification of the mixing process where the vessel is rocked along its longitudinal axis.

FIG. 19A illustrates a further alternative to induce the contents of the vessel 10 through perforations in septum 500 by rocking the vessel 10 as shown by arrows 1901, 1902. A conventional rocking-type system is illustrated in of U.S. Pat. No. 6,544,788, herein incorporated by reference in its entirety.

Figure 19B:
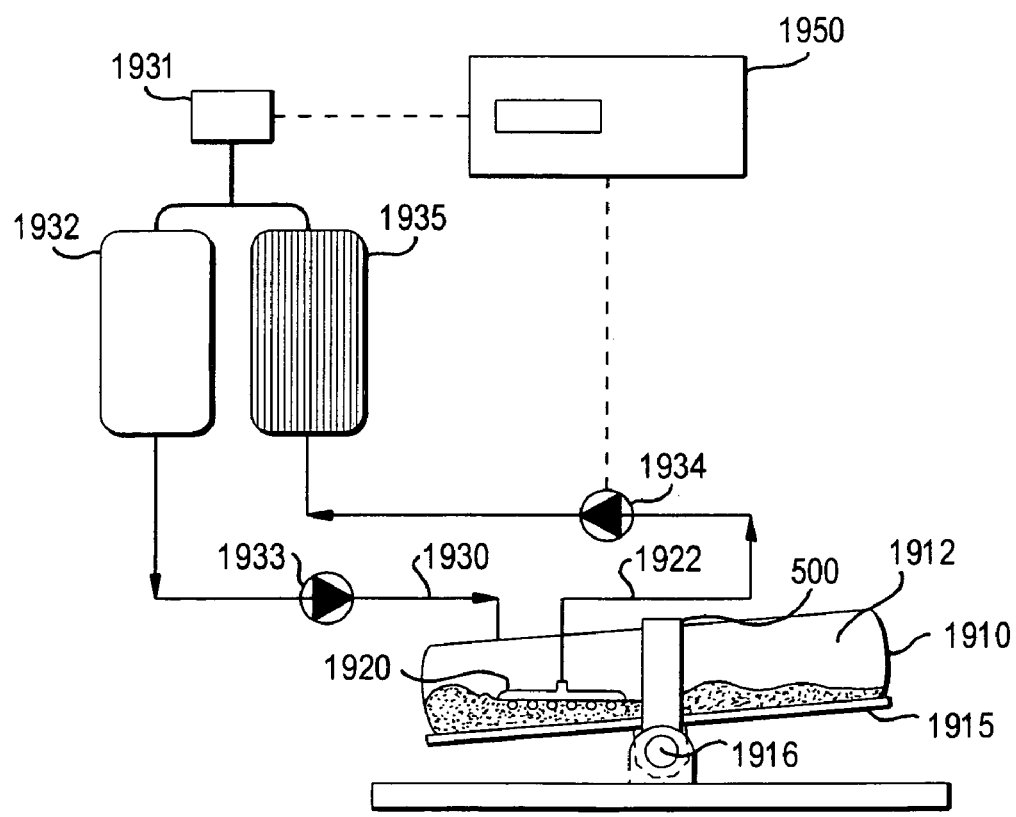
FIG. 19B shows a different embodiment of a rocking vessel.

As shown in FIG. 19B, one embodiment of the present invention consists of a plastic bag 1910 that can be partially (10% to 80%) filled with, e.g., culture media and cells. The remainder of the chamber is typically inflated and can have a gas filled headspace 1912. Oxygen, necessary for cell metabolism, can provided by air (or other oxygen enriched gas) can be introduced through sterilizing inlet filter 1913 (not shown), or otherwise introduced before the container is sealed. Exhaust air can be vented from the chamber, (if necessary) through an exhaust filter 1914 (not shown). This filter 1913 can be modified to ensure that no cells can be released as an aerosol from the bioreactor. It can also be use to ensure that in the event of bag depressurization, backflow through the vent 1914 would not result in contamination. The bag 1910 can attached to a rocking platform 1915 that can moves back and forth, e.g., across pivot point 1916. Typical rocking speeds can be at any rate from 5 to 100 rocks per minute, typically 5 to 75 rocks per minute and preferably 10 to 30 rocks per minute through any angle, typically 1 to 25 degrees from the horizontal, typically 2 to 15 degrees, and preferably 4 to 10 degrees from the horizontal.

The perfusion filter 1920 can floats on the liquid surface. It is preferably constructed such that it has essentially neutral buoyancy. The lower surface of the filter 1920 can include a liquid permeable membrane 1921 (not shown) that is submerged in the liquid during use. This membrane 1921 preferably has a porosity such that cells cannot pass through it. By applying suction on a the flexible filtrate tube 1922, cell-free filtrate is drawn up into the filter 1920 and removed from the bioreactor. The flexible tube 1922 is the only attachment point of the filter 1920 and so the filter 1920 is free to move on the liquid surface. The rocking motion of the bioreactor can move the filter back and forth rapidly across the liquid surface. This rapid tangential movement of the filter 1920 on the surface can be used to exert a scouring action and keeps the filter 1920 from clogging.

The perfusion filter 1920 preferably includes a filtration membrane, made of a material of suitable porosity to retain cells. In the preferred embodiment, the filter membrane can be a sintered porous polyethylene sheet with a mean pore size of 7 microns (Porex T3). The porous polyethylene has the advantage of a very smooth surface and is electrically charged such that the cells are inhibited from attaching to the surface of the filter 1920. The polypropylene material can also be easily heat welded. Other suitable plastics such as nylon and polyethylene could also be used. The filtration membrane is preferably heat welded to a non-porous upper layer. In the preferred embodiment this layer is made of clear polyethylene film. A hose barb port can be attached to the upper layer so that the filtrate tube may be easily attached. A polyethylene mesh can be placed inside the filter 1920 to prevent the filtration membrane from being sucked flat against the upper layer and choking off flow. The entire filter assembly 1920 can be sealed by a thermally welded seam.

The filter 1920 is placed inside the bioreactor bag and a harvest tube 1922 is connected using flexible tubing so that the filtrate can be removed from the bioreactor. It is preferable that this tubing be flexible enough to permit the filter 1920 to move freely on the liquid surface. The filter 1920 and bioreactor bag can be sterilized in situ by gamma radiation. The system is extremely simple to use—the bag 1910 is filled with growth promoting sterile nutrient media. Cells can be added and the bag 1910 placed on the rocking platform 1915. The bioreactor is rocked and aerated to promote cell growth. Once the cell density has reached the desired level (typically 2 to 4 million cells/ml) perfusion operation is started. Cell-free filtrate is withdrawn through the perfusion filter 20 and collected. Equal amount of feed is added to provide nutrients. The perfusion operation puts the cells into a steady-state operation and can be extended for many weeks. Perfusion operations require that nutrients be fed at a slow rate to the bioreactor. At the same time, liquid must be removed from the bioreactor to keep the volume reasonably constant and to remove toxic metabolic byproducts. In the case of secreted products, this harvest liquid may contain the product to be purified. In perfusion operation it is critical that cells not be allowed to leave the bioreactor. Otherwise, the cell concentration in the bioreactor will drop due to washout of the cells. In practice, a small amount of cell loss (<10%) is tolerated in order to remove dead and dying cells and to promote a low level of cell regrowth. Although a single filter 1920 is shown, multiple filters, such as one on either side of the septum or multiple filters on the same side of the filter may be used.

A preferred perfusion control system according to the present invention is shown in FIG. 19B. The bioreactor is typically fed nutrients from a feed container 1932 that can be suspended from a hook equipped with a weight sensor 1931. The rate of feed can be controlled by a feed pump 1933. This feed pump 1933 can be operated intermittently by a controller 1950 pumping feed into the bioreactor via inlet port 1930. The controller 1950 can turn the feed pump 1933 on until preset weight of feed, as measured by loss in weight of the feed container 1932, is delivered into the bioreactor. Next, the harvest pump 1934 can be switched on. This pump 1934 can be use to suck filtrate up through the perfusion filter 1920 and pump the collected material into a collection vessel 1935, which is also typically suspended from the same hook as the feed container 1932. The controller 1950 typically runs this pump 1934 until the net weight loss measured at the hook is zero, i.e., until the mass of the material added to container 1935 equals the mass of the material removed from container 1932. This ensures that the amount of harvest removed equals the feed added to the bioreactor. The cycle can then be repeated. The frequency of cycling can be adjusted to give the desired overall perfusion rate. The cumulative amount of feed added and harvest removed can be easily calculated from the cycling of the weight sensor 1931. This simple mechanism provides complete control of feed rate and harvest. Alarms can be programmed to warn of pump or filter failure to prevent the loss of valuable cells.

Figure 5:
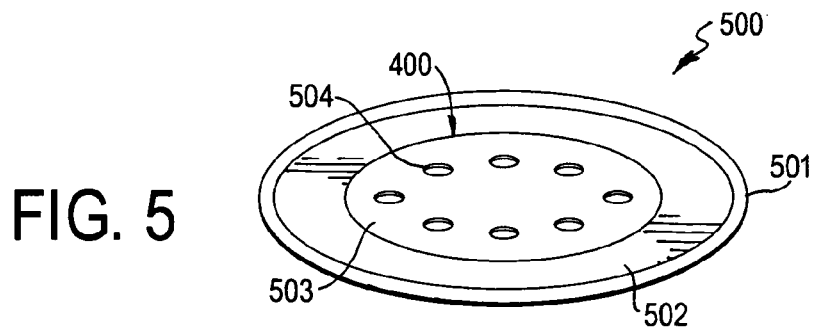
FIG. 5 illustrates a septum of the vessel shown in FIG. 3.

A more detailed view of a typical septum 500 according to the invention is shown in FIG. 5. The outer ring 501 of the septum has located inside it a generally flat piece of fabric 502. The portion of septum 500 that interacts with the inner chambers of the vessel has a series of perforations or holes 504, which form the perforations region. Each hole 504 is not designed to filter material, but is intended to create a flow pattern and generate turbulence as the material passes through septum 500 which aids in the mixing and other processes using the septum. The shape, size, and edge properties (along with septum velocity) can be modified to change the fluid shear properties (e.g., low for cell matter, and high for chemicals requiring aggressive mixing).

Figure 6C:
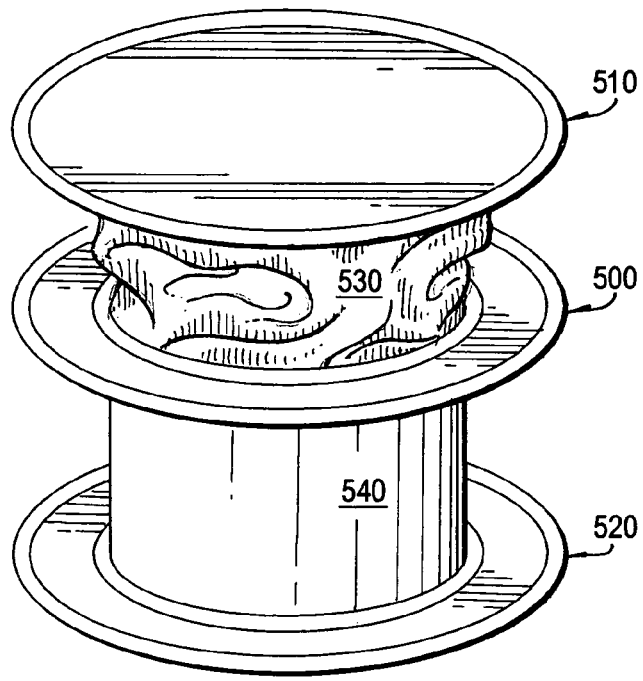
FIG. 6C illustrates the vessel shown in FIG. 3 filled half full with the gas head partially removed.

A mixing operation of vessel 10 is shown in FIGS. 6A, 6B and 6C. Generally, material 1 to be mixed is introduced into vessel 10 via an entrance tube 570 located in upper disk 510. Vessel 10 is filled up to about its midway point of its full volume to allow for flexing of the vessel. Following the introduction of material 1 into vessel 10, entrance tube 570 is closed. For most operations, a vacuum is then applied to vessel 10 via vacuum tube 550 to remove excess air and bring upper disk 510 down against the material 1 level in the vessel. The removal of the air creates a run length of wrinkles in the vessel sidewalls that allows septum 500 to move relative to each of upper and lower disks 510 and 520. The removal also prevents gas entrainment is the mixing process. However, some operations allow for the excess air and other gases to remain in vessel 10. For example, some reactions require the absence of air or oxygen and, thus, an inert atmosphere (such as nitrogen, a noble or other inert gas) can be placed in the vessel 10 both during filling and during subsequent mixing or other use of the vessel 10.

In one embodiment, the mixing operation comprises a motion of septum 500 between two positions as shown in FIGS. 6A and 6B. In the first position, septum 500 is pulled nearly into contact with upper disk 510 allowing for nearly all of material 1 to be in the lower chamber of vessel 10. The lower wall 540 is tightened as a result and holds the bulk of material 1. Such is shown in FIG. 6A. A perspective view of vessel 10 at this position during a mixing motion is shown in FIG. 6C where the vessel is half full of material 1 with the gas partially removed and lower wall 540 is tightened while upper wall 530 is wrinkled as septum 500 is pulled upwards. The motion can be generated by any means, such as manual, pneumatic, hydraulic, magnetic or any other electromechanical system, such as by pistons 2020, 2021 located 1800 apart and connected to the periphery of septum 500.

Figure 20:
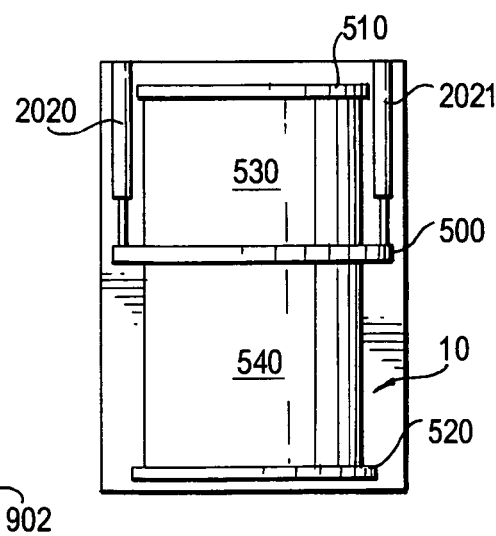
FIG. 20 illustrates the use of two pistons connected to the septum to provide movement of the septum through the contents of the vessel.

In the embodiment of FIG. 20, upper disk 510 and lower disk 520 are reaction plates and septum 500 is attached to a center drive actuator (shown as pistons 2020 and 2021). Herein, flexible vessel 10 is mounted to the reaction plates 510 and 520 as well as to the drive actuator plates. As shown in the various figures, each of these plates may be secured to the material of the vessel 10 by a deadman. Alternatively, the septum 500 may be connected to the vessel via a rigid, hard connection. In order to allow independent squeezing and expanding of the plates, reaction plates 510 and 520 may be provided with separate motion. Furthermore, by mounting septum 500 on a separately actuated drive mechanism, greater flexibility is provided, allowing pressure against one or both reaction plates 510 and 520. Such further flexibility includes the application of various processing parameters, e.g., force, range of motion, temperature, and vacuum/pressure. Moreover, fill/discharge tubes 2025 may be included to allow for easy filling or emptying of the vessel. While vessel 10 is shown with two fill/discharge tubes on top and one on the bottom, it is within the scope of the invention to vary the numbers and location of the various tubes 2025. For example, the tubes 2025 may be placed on the sides of the vessel in any combination. Additional mechanisms may be provided to rotate the vessel in one, two or all three axes. Because the mechanical actuator may be separated from the contents of the vessel, CIP/SIP is not needed. Finally, the mechanical actuator may be programmed to accomplish any number of functions, such as mixing, reacting, and filtering.

Then septum is pulled downwards towards lower disk 520. During this operation, both the upper wall 530 and lower wall 540 would be wrinkled. As it is pulled, material 1 begins to pass through holes 540 in the perforation region 400 and begins to enter the upper chamber of vessel 10. Holes 540 create a rapid flow of material 1, forcing the mixture of the constituents of material 1 and then injecting material 1 into the upper chamber to create a turbulent flow in the material, further aiding mixing of the constituents. Once septum 500 is pulled completely down near lower disk 520, nearly all of material 1 is located in the upper chamber. This situation is shown in FIG. 6B.

The mixing process is then continued by pulling the septum upwards towards upper disk 510, which is a reverse operation to that described above, and results to achieve the situation shown in FIG. 6A again. A full mixing operation comprised of multiple operations of this movement of septum 500 up and down will thoroughly mix the constituents in material 1. Following completion of the mixing process, the material can be either stored within vessel 10 or discharged into another location.

In an additional embodiment, septum 500 can be used as a conductive heating/cooling source to heat or cool material 1 located within vessel 10. In FIGS. 7A and 7B, a temperature tube 703 is run through the middle layer of fabric of septum 500. Tube 703 may be a simple flute hole extending into septum 500. Tube 703 may also be a chamber formed throughout septum 500, in between upper septum layer 705 and lower septum layer 706. A baffle 704 is then connected to an outer portion of septum 500 to divide temperature tube 703 into two channels or chambers, an upper channel 708 and a lower channel 709, except at a connection hole 707, which communicates the upper and lower channels. At an outer fabric ring 505 of septum 500, a temperature fluid entrance tube 701 is connected to the septum and communicates with one channel of temperature tube 703 and a temperature fluid exit tube 702 is connected to the other channel of the temperature tube. Fluid introduced into temperature fluid entrance tube 701 travels along upper channel 708 through temperature tube 703, down through connection hole 707 into lower channel 709 through the temperature tube and exits at temperature fluid exit tube 702. Such creates a fluid circuit within septum 500, as shown in FIG. 7B. If a hot fluid in sent through the circuit, the fluid will heat up septum 500, and septum 500 will transfer the heat into material 1 in vessel 10. Likewise for cold fluid sent through the circuit. While this conductive heating/cooling operation may be operated alone, it is preferably operated in conjunction with a mixing motion of vessel 10 as outlined above to provide a more effective process. The conductive heating/cooling process may also be operated simultaneously with a mixing operation.

As an alternative to the fluted heating system as disclosed above, septum 500 may have a heating/cooling system extending throughout its inner chamber, which is shown in FIGS. 7C and 7D. In such a design, septum 500 comprises a pair of parallel rigid plates 730 and 740 in lieu of the flexible material of the other embodiments. Running between rigid plates 730 and 740 is a baffle plate 720 which creates a septum upper chamber 731 and a septum lower chamber 741 between the rigid plates. In a process of heating or cooling, fluid enters septum 500 via the temperature fluid entrance tube 701 and passes into septum upper chamber 731. The fluid spreads throughout septum upper chamber 731 which allows the temperature of the fluid to dissipate into the material in vessel 10. The fluid then passes through central passage 710 and into septum lower chamber 741, where the fluid again spreads throughout the septum lower chamber which allows the fluid temperature to further dissipate into or out of material 1 in vessel 10. The fluid then exits septum 500 through temperature fluid exit tube 702 where the fluid can be recycled and recirculated through the septum. This process can also be completed while performing a mixing or other process. The plates 730 and/or 740 can be formed of metal, plastic, ceramic, composites or similar materials.

Figure 8:
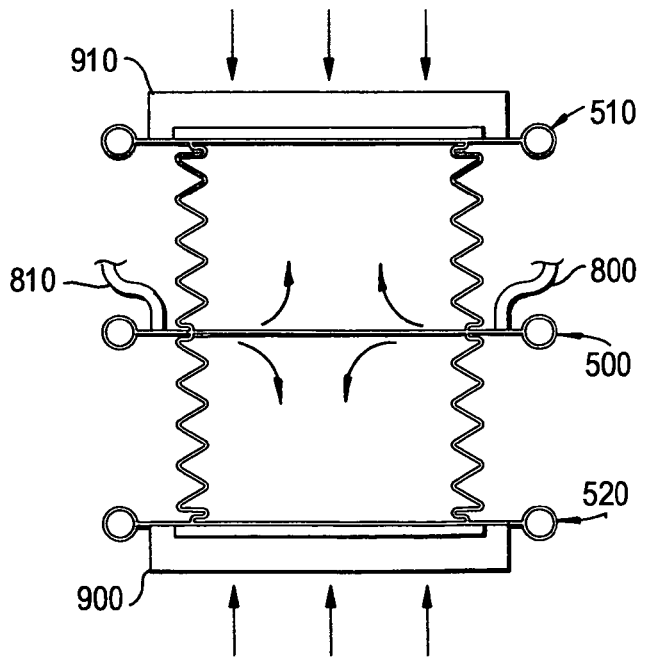
FIG. 8 illustrates a cut away view of the vessel according to another embodiment of the invention having means for a reacting material.

As a further alternative to the conductive heating processes described above, a pair of reaction plates 900 and 910, as shown in FIG. 8, e.g., can be attached to vessel 10 against upper and lower disks 510 and 520 may provide, e.g., microwave heating during mixing or other operations. Reaction plates 900 and 910 may have microwave emitters incorporated therein or attached thereto which can be used to heat up material 1 inside the chambers of vessel 10 through either the top or bottom surface of the vessel. Inductive heating of the septum can also be achieved through the use septums made of metal.

FIG. 8 additionally shows a frangible bag 890 which can contain material. By utilizing a frangible bag 890, the material can be maintained separated from the septum and any other material. Only upon rupturing of the bag 890 is the material contained therein released. Such rupturing may be accomplished by physical pressure (such as squeezing), chemical, heat or any other means. Such frangible bags 890 may be utilized in any embodiment described herein. Similarly, the septum 500 may be provided with a frangible element, such as a membrane, which essentially accomplishes the same purpose as the bag 890. Upon rupturing of the membrane, can the contents of the vessel contact each other and the septum. Such a membrane may be ruptured in the same or a different manner than the bag 890.

Figure 9A:
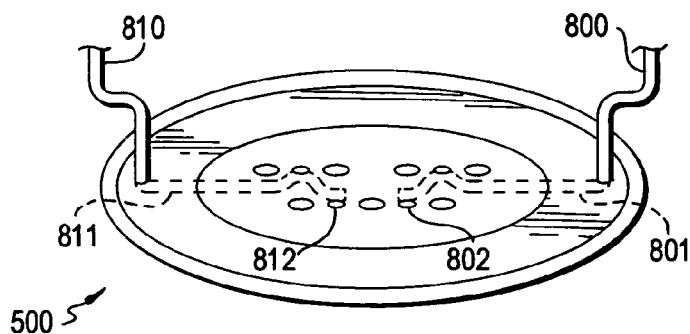
FIGS. 9A and 9B illustrate another embodiment of the septum having additional means to add other materials into the vessel for fermentation or other processes.
Figure 9B:
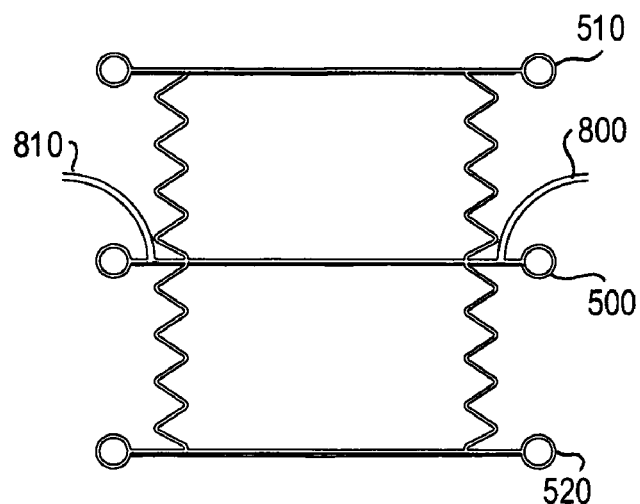

In another embodiment, vessel 10 may be operated as a bioreaction, such as fermentation, apparatus. The apparatus has additional feed tubes 800 and 810 interconnected to septum 500 and intercommunicating to the inner chambers of vessel 10, as shown in FIGS. 9A and 9B. Feed tubes 800 and 810 communicate, at the outer fabric ring 505 of septum 500, with inner feed tubes 801 and 811, respectively, which in turn communicate with the inner chambers of vessel 10 through feed holes 802 and 812, respectively. At or near feed holes 802 and 812, within inner feed tubes 801 and 802 or even within feed tubes 800 and 810, are one way valves for preventing a back wash of material from the inner chambers out the feed tubes. Such features provide the ability to add material, chemicals or gas into the chamber during mixing, reacting or heating operations of vessel 10.

The process of bioreaction begins with a media pre-mixing, heating and cooling, which may take place within vessel 10 or other similar vessels. Then the correct proportions of media and seed are introduced into vessel 10 via the method described above. Then it is determined whether a gas head is desired within the chambers of vessel 10, for example, introduce or leave a gas head if needed for an aerobic reaction, remove head if anaerobic. If no gas head is desired, then the gas head is pulled from vessel 10 via the method described above. The entire material 1 is then mixed, cooled and heated as needed using the methods and apparatus described above and continued as necessary.

Addition of make-up solutions, optionally including a gas, are then added as needed through feed tube 800 and into the chamber through inner feed tube 801 and feed hole 802. These solutions can be metered in septum 500 or before they are introduced into the septum. Such process allows for efficient introduction and mixing with minimal agitation. At the proper point, the lysing solution can also be added into the chamber via feed tube 810, inner feed tube 811 and feed hole 812. These solutions can also be metered through the septum or externally, optionally through individual feed tubes. Following the process, the meter solutions can be either stored within vessel 10 or discharged into another location.

In another embodiment, vessel 10 operates as a reactor for constituents of material 1. As mentioned above, vessel 10 is provided with a pair of reaction plates 900 and 910. These plates, in addition to providing a heat source for vessel 10, also move with respect to each other to provide pressure against vessel 10, as shown in FIG. 8. The pressure effectively squeezes vessel 10 to aid in promoting a chemical reaction, while still allowing mixing to occur.

The process begins by adding in constituents, such as separated or pre-mixed powders, solvents, etc. along with catalysts, into the chamber of vessel 10 in the method as described above and in reference to FIGS. 8, 9A and 9B. If needed, as also described above, gas head may be removed via vacuum tube 550. The gas head can also be maintained if needed. Once these constituents are added in and vessel 10 is sealed, reaction plate 900 and 910 begin to apply pressure and begin to squeeze the vessel. Catalysts may be added by introducing them through feed holes 802 and 812. Catalysts may also be captured on the center septum such that they would contact material 1 during a mixing operation. Catalyst may also be introduced along the perforations in the septum, especially when the system is made of metal. The constituents along with the catalysts are forced together to a predetermined pressure that is required for the specific process or material desired. Additionally, the material may be heated or cooled in the manner as described above via either septum 500 or the microwave or other heaters associated with reactors 900 and 910. The mixing process may also be performed simultaneously with the pressure to aid in the reacting process. Following completion of the reaction process, the material can be either stored within vessel 10 or discharged into another location.

Figure 10A:
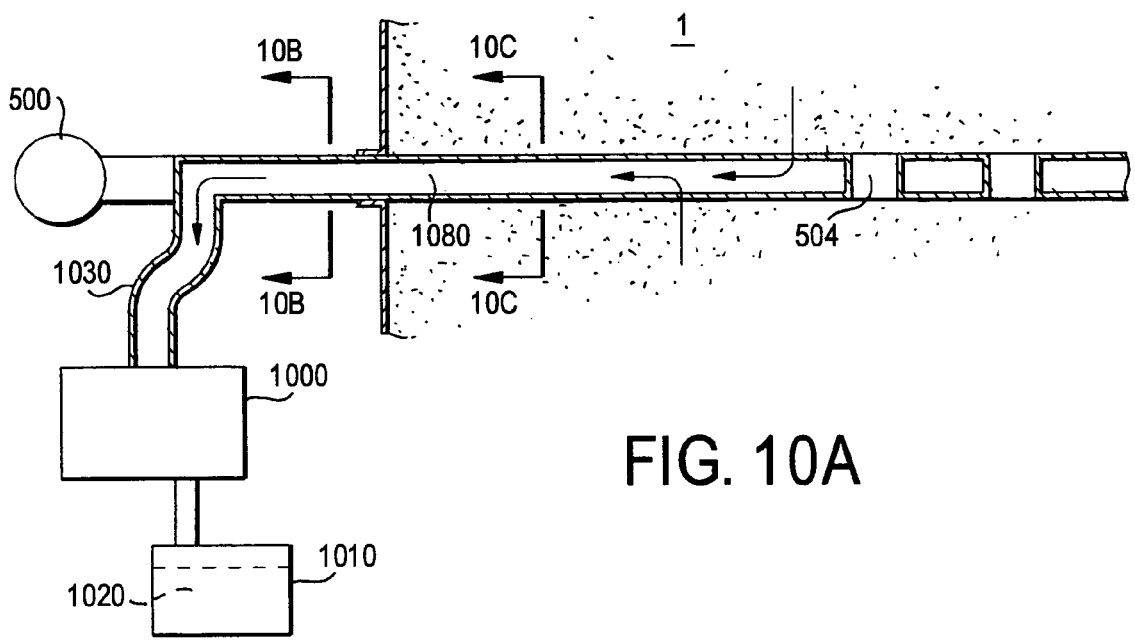
FIG. 10A illustrates another embodiment of the septum incorporating a micro/ultra-filtration system.
Figure 10B:
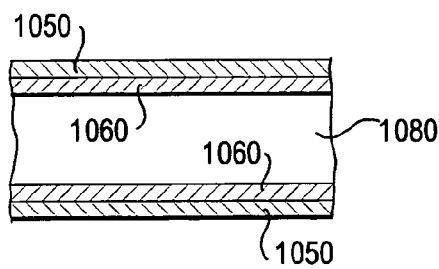
FIG. 10B illustrates a cross sectional view of the septum shown in FIG. 10A along line 10A-10A.
Figure 10C:
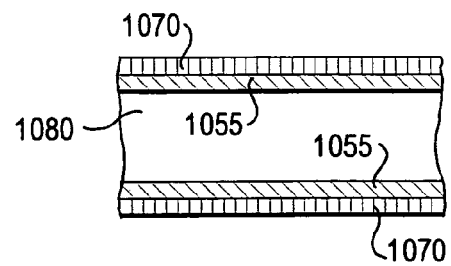
FIG. 10C illustrates a cross sectional view of the septum shown in FIG. 10A along line 10B-10B.

In a further embodiment, vessel 10 can have incorporated therein a micro/ultra-filtration system. As shown in FIGS. 10A, 10B and 10C, septum can have a plurality of filter regions and mixing regions. In side the chamber of vessel 10, the fabric of septum 500 has various filter regions, and within each region, septum 500 has on its outer surface a micro-porous coating (filter) 1070 for filtering material, a structural fabric 1055 beneath the coating and a spacer fabric layer 1080 inside these layers which allows for trapping and movement of filtered material. Outside vessel 10, in the region of the outer fabric ring 505, septum 500 has a non-porous sealant layer 1050 re-enforced with a structural fabric 1060 for preventing leakage of filtered material from outside septum 500 and another spacer fabric layer 1080 for trapping and movement of filtered material. The spacer fabric layers 1080 effectively provide a transit tube by which the particulate is moved to outside vessel 10.

Communicating with spacer fabric layer 1080 is a filter tube 1030 that is further connected to a vacuum source 1000 which provides a vacuum through the system to pull in particulate from material 1, through the micro-porous coating 1070, into the spacer fabric layer 1080 and into and through the vacuum. Vacuum 1000 then deposits filtered particulate 1020 into a filtrate container 1010. A vacuum of 11 to 13 psi provides a generally sufficient vacuum for microfiltration, however, other vacuums may be used depending on the application.

For an effective filter operation, a mixing process may be used in conjunction with the vacuum applied across the filter. The mixing process creates turbulent flow conditions and performs a recirculation function as outlined above which keeps the level of particulate even throughout the material 1 in vessel 10 and prevents fouling of the micro-pores by larger particles. As the particulate in the material 1 nears moving septum 500 during a mixing operation, the vacuum will pull it from the material into the vacuum system. Alternatively, the pressure drop across the micro-porous coating can be achieved by pressurizing material 1 in vessel 10 using reaction plates 900 and 910, describe above, to squeeze vessel 10.

Figure 13A:
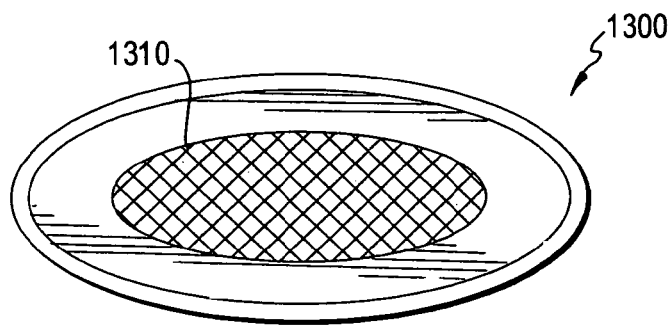
FIGS. 13A-13C illustrate a septum and a cut-away view of the vessel according to another embodiment of the invention showing a system and method for microfiltration of material.

As an alternative to this filtration system, vessel 10 may have incorporated therein a filter septum 1300 in addition to septum 500, as shown in FIG. 13A. Rather than a septum having the features described above, filter septum 1300 has a micro-filter 1310 located therein to filter out a predetermined material. The filter septum 1300 is preferably located between septum 500 and lower disk 520, as shown in FIGS. 13B and 13C, but other locations are possible.

Figure 13B:
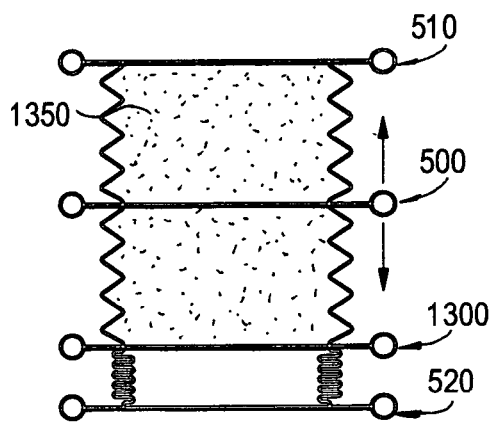
Figure 13C:
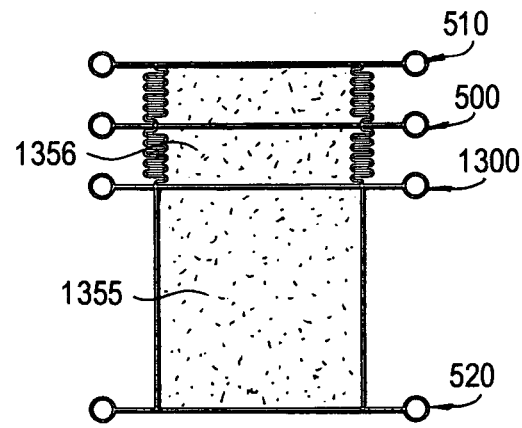

A preferable process of filtration using filter septum 1300 begins by lowering filter septum 1300 until it is adjacent to lower disk 520, as shown in FIG. 13B. Then other process described herein may be performed, such as mixing, heating/cooling, reacting and/or fermenting. Following these processes, septum 500, can be operated in a mixing mode while filter septum 1300 is then pulled up while septum 510 is held stationary, e.g., until it is adjacent septum 500 and both septums are pulled adjacent to upper disk 510. This creates a pressure that forces material 1350 through micro-filter 1310, leaving a retained material 1356 above filter septum 1300 and a residual material 1355 below. The continued mixing operation of septum 500 during the filtration provides turbulent flow conditions needed for efficient filtration.

In another embodiment of the invention, vessel 10 can be used to express slurry 1150 into a cake. As shown in FIGS. 11A through 11E, vessel 10 has a flexible spacer fabric layer 1110 and a cake fabric filter 1120 which provides means to filter the cake from the slurry 1150 or to filter the cake from a cleaning agent. Additionally, vessel 10 has an isolation film 1130 with a tear bead 1131. The isolation film allows for the mixing, heating/cooling, reacting and/or fermenting to create slurry in the chamber of vessel 10 without interfering with cake filter 1120 and exiting out slurry tube 1100.

A bag out sleeve 1140 provided along side wall 530 which allows a user to reach into the chamber of vessel 10 and pull tear bead 1131 and remove isolation film 1130 from the surface of spacer fabric layer 1110 and cake fabric filter 1120.

Figure 11A:
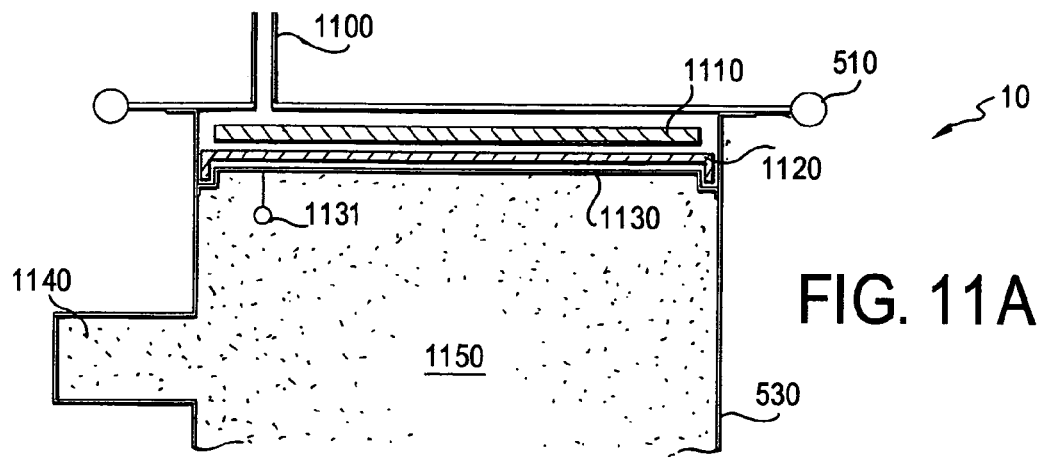
FIGS. 11A-11E illustrate a cut-away view of the vessel according to another embodiment of the invention showing a system and method for making and cleaning cakes from a slurry.
Figure 11B:
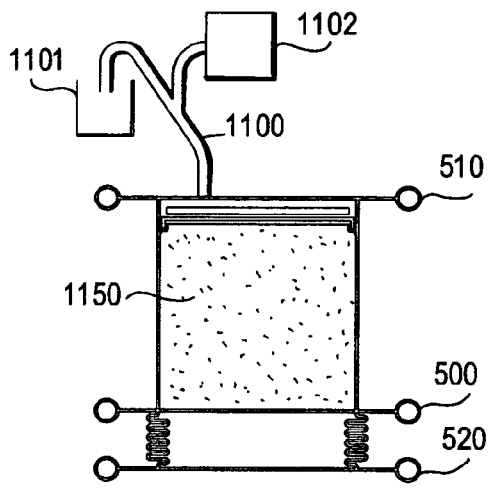
Figure 11C:
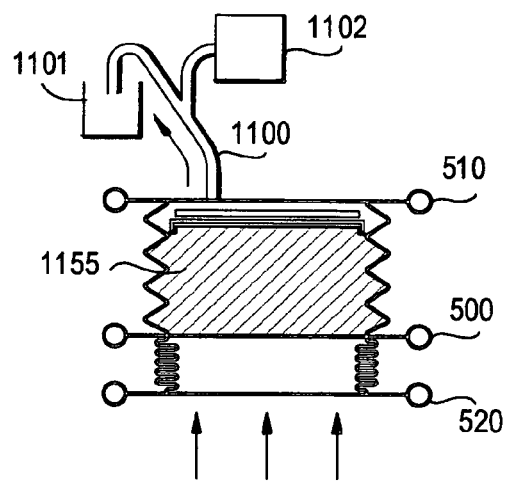
Figure 11D:
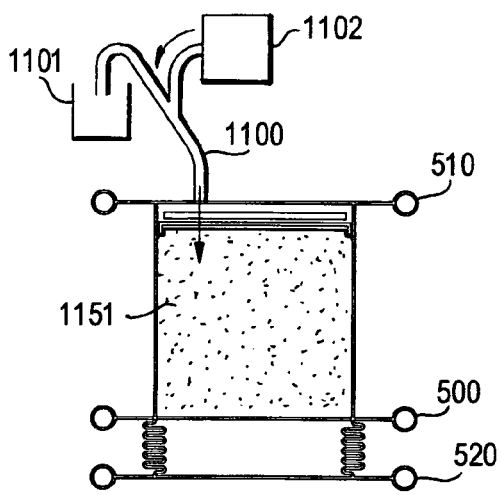
Figure 11E:
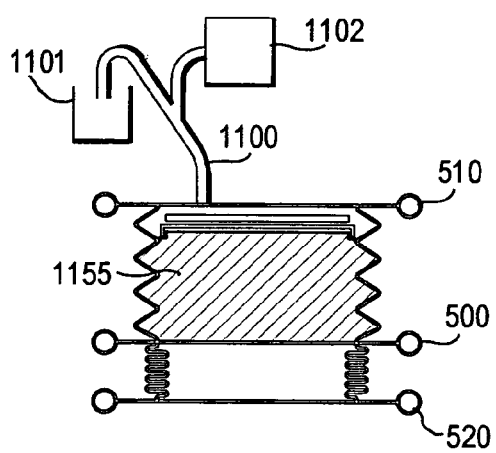

A process of creating a cake using vessel 10 is shown in FIGS. 11B and 11C. First, slurry is created inside the chamber of the vessel 10 using a process outlined above or is placed into the chamber via entrance tube 570 (FIG. 6A) and any gas head may be vacuumed out via vacuum tube 550 (FIG. 6A). Septum 500 is moved downward into contact with lower disk 520. Next, isolation film 1130 is removed by pulling tear bead 1131 via bag out sleeve 1140 to allow filtration of slurry 1150.

To begin expressing a cake from slurry 1150, septum 500 and lower disk 520 are moved upwards towards and against upper disk 510. Such motion forces the slurry into cake filter 1120 which prevents cake particulate from passing and allows a slurry discharge to exit the chamber of vessel 10 through slurry tube 1100. The slurry discharge is collected in a discharge collector 1101. Lower disk 520 and septum 500 will continue movement upwards until all possible slurry discharge is removed from now forming cake 1155, as shown in FIG. 11C.

Following an expressing step, it may be desired to clean cake before any further processing. In such a process, a cleaning solution is injected into the chamber of vessel 10 from cleaning apparatus 1102 and through slurry tube 1100 while simultaneously pulling septum 500 and lower disk 520 downward and away from upper disk 510. The chamber will now have cake particulate and a cleaning solution therein. A mixing motion may then be performed to thoroughly clean and mix the cake particulate and the cleaning solution into cleaning slurry 1151. Heating or other process may also be performed.

Once the cake particulate is thoroughly cleaned, the cleaning solution is removed from the chamber by pulling up septum 500 and lower disk 520 towards upper disk 510. The cleaning solution is forced through cake filter 1120 which filters out the cake particulate. The cleaning solution is then collected in the discharge collector 1101. Upon full removal of the cleaning solution, a cleaned cake 1155 is formed in the chamber of vessel 10.

Following creation of cake 1155, lower disk 520 is retracted to its lower most position away from upper disk 510. Upon a vibration of the upper disk area, the cake 1155 will fall to the bottom of vessel 10 adjacent lower disk 520. Following this process the cake can be either stored within vessel 10 or discharged into another location.

Following a process of creating cake 1155 or introduction of the cake into vessel 10, the vessel may also be used to dry the cake using components of the vessel outlined above with an additional drying septum 1220 having a wire grid and/or a fabric grid incorporated therein, as shown in FIGS. 12A through 12D. While an additional septum may be used, its features may be incorporated into septum 500 for use in vessel 10. For simplicity sake, whether an additional septum is used or drying septum 1220 is used, FIGS. 12B through 12D will show only drying septum 1220.

The drying may be completed using two separate systems of drying. First, reaction plate 900 may be located adjacent below the upper or lower disks 510 and 520. Reaction plate 900 below lower disk 520 is shown. Reaction plate 900, as described above, has incorporated therein a microwave heater which can be use to heat cake 1155 located within the chamber of vessel 10. Additionally, a gas may be introduced into vessel 10 via gas tube 1210 to interact with cake 1155 and then the moisture laden gas exits vessel 10 via gas exit tube 1220.

Figure 12A:
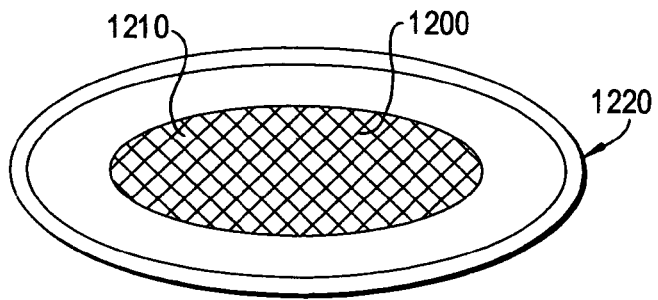
FIGS. 12A-12D illustrate a septum and a cut-away view of the vessel according to another embodiment of the invention showing a system and method for drying cakes.
Figure 12B:
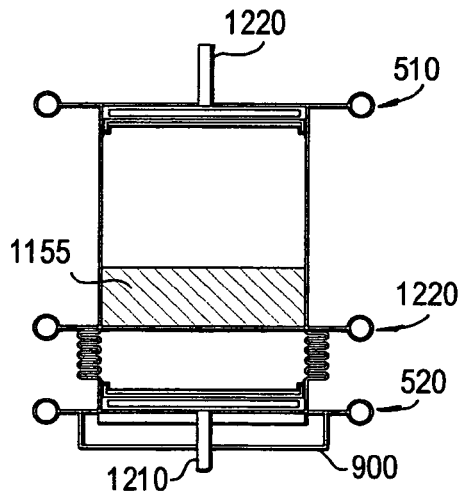
Figure 12C:
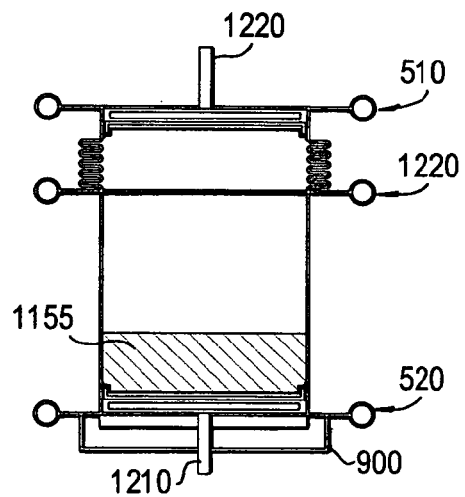
Figure 12D:
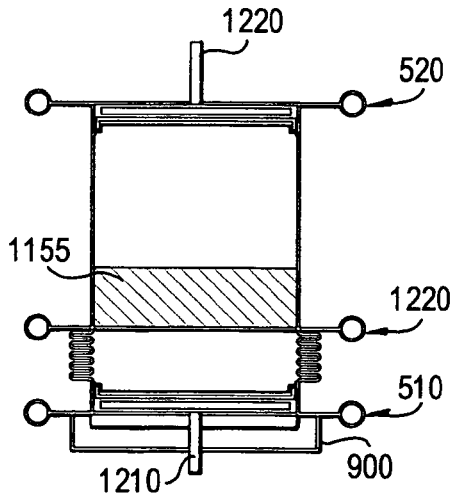

A process for drying cake 1155 is shown in FIGS. 12B through 12D. Cake 1155 is introduced into vessel 10 via any means previously disclosed or cake is formed by the process disclosed above. Drying septum 1220 is placed adjacent lower disk 520 and both are pulled away from upper disk 510, as shown in FIG. 12B. Microwave heat is then applied to cake 1155 by reaction plate 900. Alternatively, heated gas can also be introduced via gas tube 1210, passed through cake 1155 and exits gas exit tube 1220. After a predetermined time, drying septum 1220 is pulled up to upper disk 510 away from lower disk 520, allowing cake 1155 to be sifted through the drying septum, as shown in FIG. 12C. After a second predetermined time, vessel 10 is then rotated over as shown in FIG. 12C. Again after a predetermined time, drying septum is pulled up, this time toward lower disk 520 away from upper disk 510. After a predetermined time again, vessel 10 is rotated again, returning it to the orientation shown in FIG. 12B. This process may be repeated as necessary to dry cake 1155. Following this process the dried cake can be either stored within vessel 10 or discharged into another location.

Figure 14A:
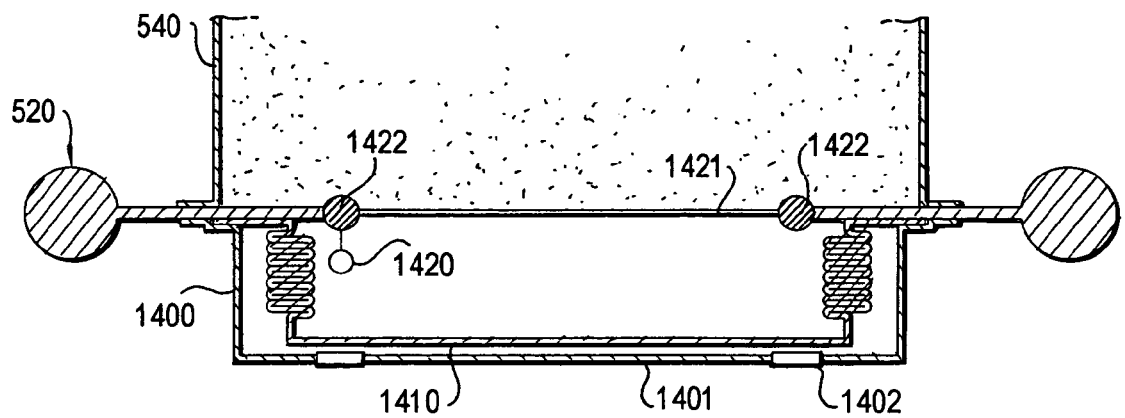
FIGS. 14A-14B illustrate a discharge means for the vessel according to the invention.
Figure 14B:
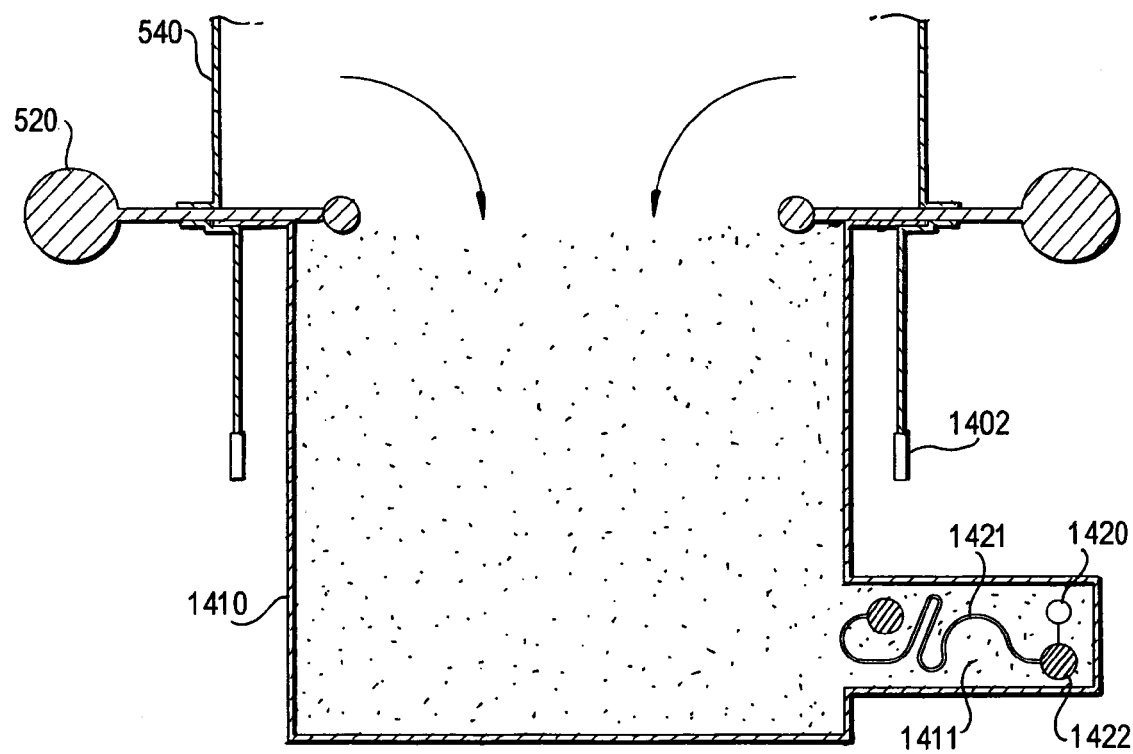

To remove material, cakes, etc., vessel 10 is provided with a discharge chute that allows removal from either upper disk 510 or lower disk 520, preferably lower disk 520. The main components of a discharge chute located on lower disk 520 are shown in FIGS. 14A and 14B. A tear panel 1421 having a generally round or other two-dimensional shape is located on a part of lower disk 520. A circumferential cord 1422 surrounds tear panel 1421 forming a buffer between lower disk 520 and tear panel 1421. A tug on a tear bead 1420 pulls cord 1422 and panel 147 from the surface of lower disk 520. Covering the entirety of tear panel 1421 and attached to lower disk 520 is a discharge bag 1410 in a folded condition. Covering the entirety of discharge bag 1410 and also attached to lower disk 520 is a bag cover comprising a anchoring portion 1400 and a loop 1401 located thereon holding in place a cover 1401. Cover 1401 may be a panel or it may be a strap for holding discharge bag 1410 in a flat orientation. Loop 1402 surrounds cover 1401 if the cover is a panel and is activated to allow removal of the cover. Loop 1402 may be a becket loop, however, loop 1402 may also be simply a connection means if cover 1401 is merely strap. Loop 1402 adjoins cover 1401 and the rest of bag cover 1400.

The process of removal of material from inside vessel 10 begins with an activation of loop 1402 to remove cover 1401. Loop then hangs down from lower disk 520, as shown in FIG. 14B. The removal of cover 1401 allows access to discharge bag 1410. Discharge bag 1410 is extended out of its folded condition to allow room to accept material from vessel 10. Once discharge bag is fully extended, a bag out sleeve 1411 is further extended from discharge bag 1410. A user pushes bag out sleeve 1411 into the chamber of discharge bag 1410 and reaches for tear bead 1420. A pull on tear bead 1420 causes cord 1422 and hence tear panel 1421 to be removed from lower disk 520. Tear bead 1420, cord 1422 and tear panel 1421 are then pulled away from lower disk 520 and into bag out sleeve 1411 as shown in FIG. 14B. This process then exposes material in vessel 10 to discharge bag 1410. Material may then flow directly into discharge bag 1410 or vessel 10 may be kneaded sufficiently to remove all material. Discharge bag 1410 my then be removed from vessel 10 for transport or storage of the material. The bottom of discharge bag 1410 may also have a connection port to another piece of equipment, if needed.

Figure 2:
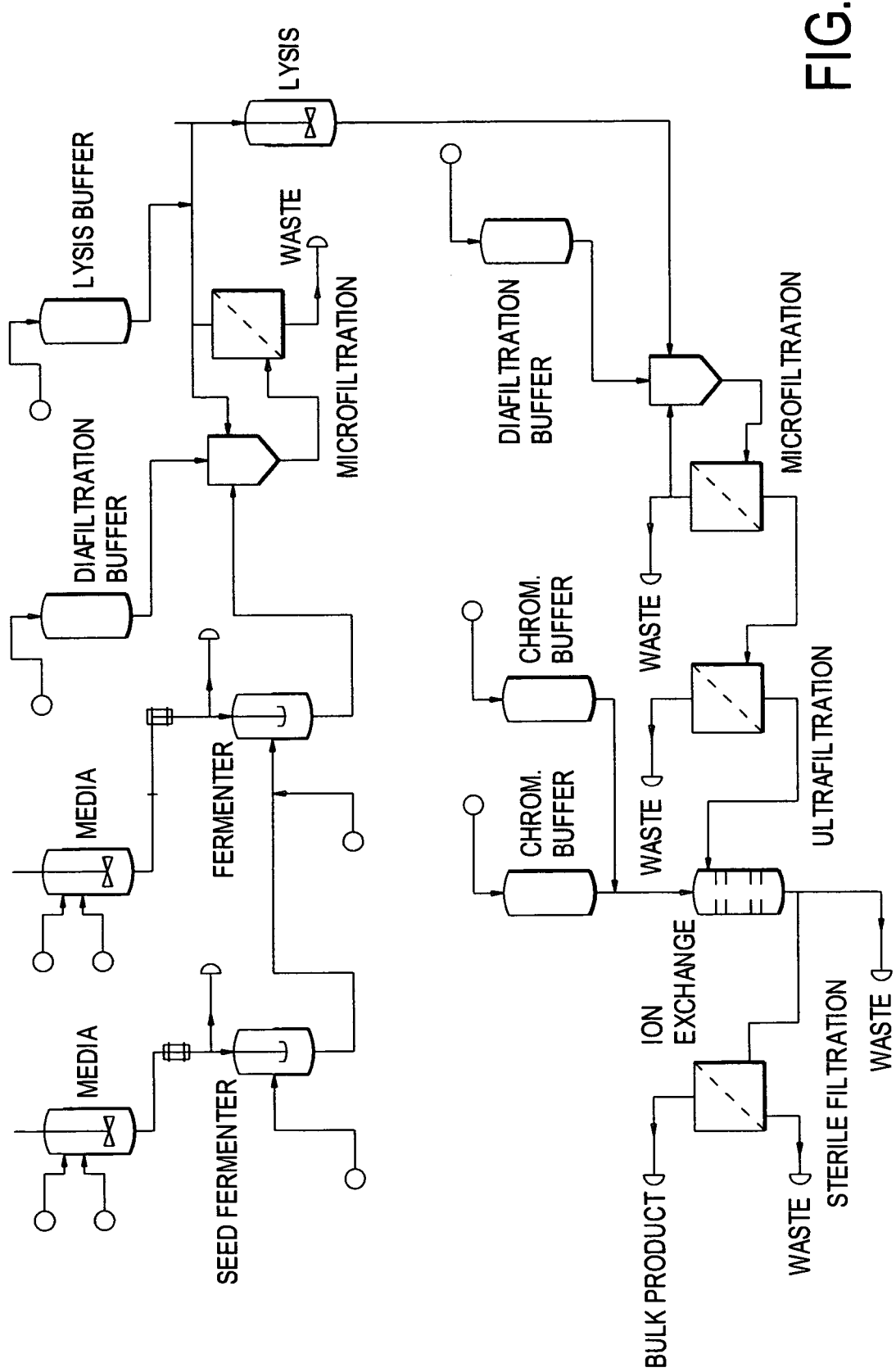
FIG. 2 is a diagram of a conventional biopharmaceutical process.
Figure 22:
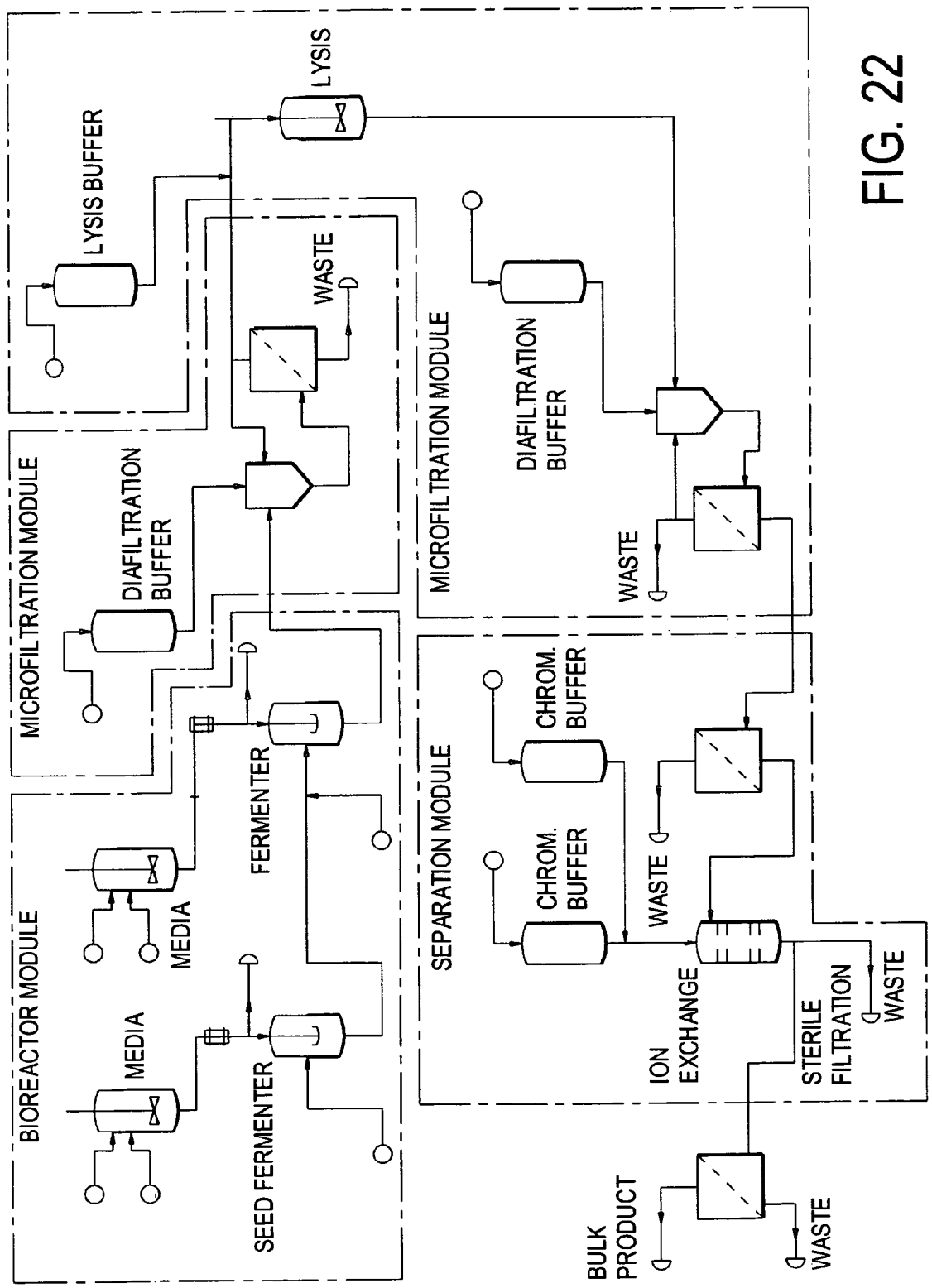
FIG. 22 is a modification of FIG. 2 showing how the invention can reduce the apparatus required in FIG. 2 to 5 modules.

Although each of the unit operations shown in a typical chemical process of FIG. 2 can be separately carried out in a vessel 10, according to the present invention a single vessel can perform multiple unit operations. Thus, as shown in FIG. 22, the process of FIG. 2 has been divided into 5 subprocess or modules shown by the dotted lines as: 1. Bioreactor module; 2. Microfiltration module; 3. Microfiltration module after Lysis; 4. Ultrafiltration module; and 5. Separation module.

As shown in FIGS. 23A-23E, the bioreactor module comprises a series of septums 2001, 2002, 2003, 2004, 2005, etc., each in a separate enclosed volume from a previous chamber created by removable isolator films 2012, 2013, 2014, 2015, etc. A tear out bead is built into such isolator films, such that when it is desired to change the unit operation, i.e., to change from a mixing operation to a filtration operation, the isolator film is ruptured permitting the mixed components to be contacted by a further septum, e.g., 2003. Other unit operations can be achieved by providing different septums and other isolating films so that progressive unit operations are all conducted in a single vessel 2013, as shown in FIGS. 23B-23E.

Figure 23A:
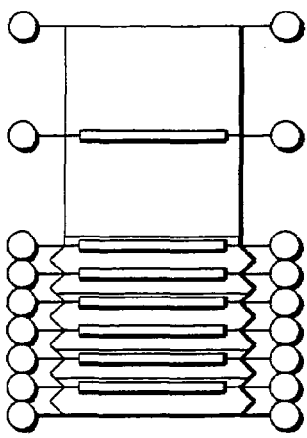
FIG. 23A-E shows the bioreactor module of FIG. 22 in detail, and at various stages of different unit operations.

FIGS. 23A-23E depict a typical operation of an embodiment of the invention. This operation is described as a preferred operation, however, the invention should not be limited to the description of this operation. With reference to FIG. 23A, media or seed is charged to the bioreactor through the top, and any gaseous head is removed by moving septum 2003 against septum 2001. Through septum 2002, the contents are stirred, heated, entrained, or measured (such as oxygen percentage) in a pH buffer. Exhaust carbon dioxide is released through the top of the bioreactor. Any replenishment media can be added through the top of the bioreactor, causing septum 2003 to move away from septum 2001 to allow for, e.g., growth in volume in the reactor.

In order to convert the bioreactor from its initial configuration, isolator film 2013 is removed, preferably through a bag out sleeve (not shown) to expose septum 2003. This converts septum 2003 from a bottom septum into a microfilter septum. Thereafter, the bag out sleeve is heat sealed and the isolator film 2012 can be discarded.

Figure 23B:
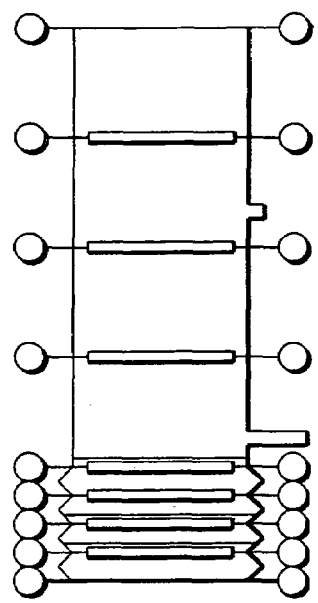

A typical microfiltation is shown in FIG. 23B, to follow the steps described with reference to FIG. 23A. A diafiltration buffer is added through septum 2002. By moving septum 2002 vertically, the contents are mixed by a turbulent flow. Septum 2003 (now a microfilter septum), is moved against septum 2001, creating pressure differential ($\Delta P$) across the septum 2003 forcing filtrate into a space B. The retentate is removed from a space A by collapsing septum 2003 and 2002 into septum 2001. Isolator film 2015 is pulled out through a bag out sleeve 2125, converting septum 2005 from a bottom septum into another microfilter septum. Thereafter, the bag out sleeve is heat sealed and the isolator film 2015 can be discarded.

Figure 23C:
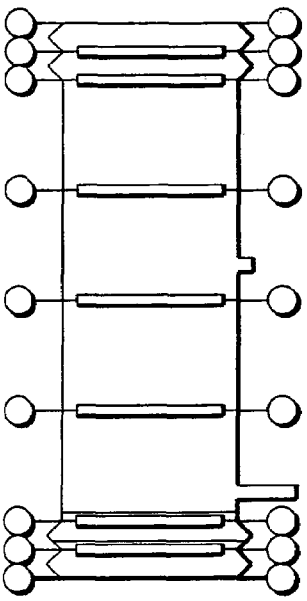

FIG. 23C depicts another microfiltration which, in this embodiment, follows the microfiltration shown in FIG. 23B. A lysis buffer is added through septum 2004, which is actually a mixing septum. Turbulent flow to mix is provided by relatively moving septum 2004 vertically. Thereafter, septum 2005 is moved against septum 2001 to create $\Delta P$ across septum 2005, forcing filtrate into a space C. Retentate is removed from space B by collapsing septums 2005 and 2004 into septums 2003, 2002 and 2001. Isolator film 2017 is pulled out through a bag out sleeve 2117, converting septum 2007 from a bottom septum into an ultrafiltration septum. Thereafter, the bag out sleeve is heat sealed and the isolator film 2017 can be discarded.

Figure 23D:
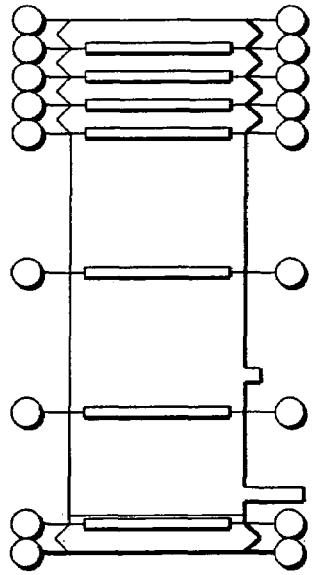

FIG. 23D shows an ultrafiltration, which in this embodiment, follows the microfiltration depicted in FIG. 23C. Turbulent flow, to mix the contents, is created by moving septum 2006 vertically. Moving septum 2007 against septum 2001 creates $\Delta P$ across septum 2007, forcing filtrate into a space D. Retentate is removed from space C by collapsing septums 2007 and 2006 into septums 2005, 2004, 2003, 2002 and 2001. Isolator film 2018 is pulled out through a bag out sleeve 2028, converting septum 2008 from a bottom septum into an separator septum. Thereafter, the bag out sleeve is heat sealed and the isolator film 2018 can be discarded.

Figure 23E:
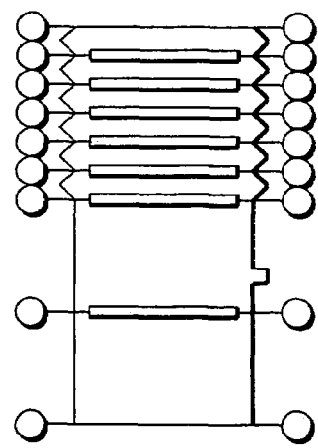

FIG. 23E shows a separation, which in this embodiment, follows the ultrafiltration depicted in FIG. 23D. Septum 2007 is moved slowly vertically until adsorption is complete. By collapsing septum 2009 against septum 2001, most of the material not absorbed is removed. Solvent is added through septum 2008 to bring the concentration to just below that necessary for desorption of the desired product. Through septum 2008, solvent and waste are removed from the bioreactor. Solvent is then added again through septum 2008 to the level to desorb the desired product. Thereafter, the solvent and the desired product are flowed out of the system through septum 2008.

Additionally, the vessels can be mounted in parallel by flexible and/or disposable piping which can be crimped off. The flow between the various vessels can be controlled, for example, by a peristaltic pump, such that metered amounts of solutions can be charged into the appropriate vessel. For example, the micofiltration system of FIG. 23B can be connected via flexible piping to a diafiltration buffer vessel on an inlet side and a containment vessel for the retentate on the outlet side. Such a system allows for containment of discharged waste as well as the product resulting from the processing, as well as completely contained charging, processing, discharging, sampling, sensing and storage.

The invention can also be used for chemical separations, such as solid phase extractions, wherein separation is traditionally based upon subtle differences in the hydrophobic attraction of the materials being separated. Small adsorbent particles are contained in a bed within a movable center septum. By moving the septum vertically, recirculation is achieved by moving the septum through the material. A preferred process for performing a solid phase extraction is as follows: (1) the material to be separated is charged into the vessel; (2) any gas volume is removed by collapsing a top septum of the vessel down to the level of the liquid; and (3) the septum is slowly raised and lowered through the material until the separation is complete. By such a system, the material moves through the adsorbent bed twice per cycle. Thereafter, the procedure follows the steps described with reference to FIG. 23E, separation. By this system, the variable volume feature allows the system to be run with less solvent.

The invention may also be used to perform a powder blending operation. According to a preferred embodiment, a center septum is initially at the bottom of a vessel, before the powders are added through the top. Air flow is used to create a fluidized bed, in from both the bottom of the vessel and through the septum, whereby the air is filtered out of the tip. Once the bed is fluidized, the septum can be moved vertically to mix or blend the contents.

Figure 15A:
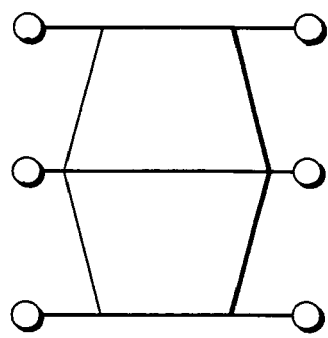
FIGS. 15A-15F illustrate differing designs and shapes possible for the vessel according to the invention.
Figure 15B:
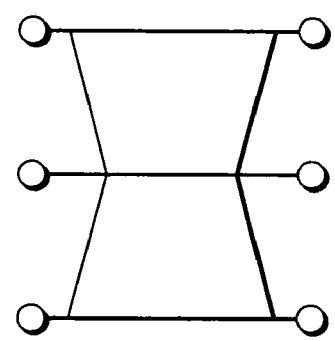
Figure 15C:
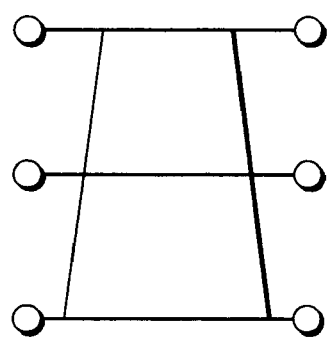
Figure 15D:
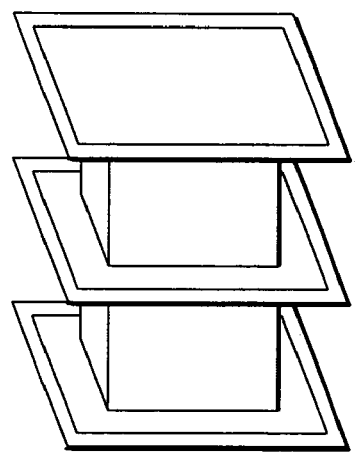
Figure 21:
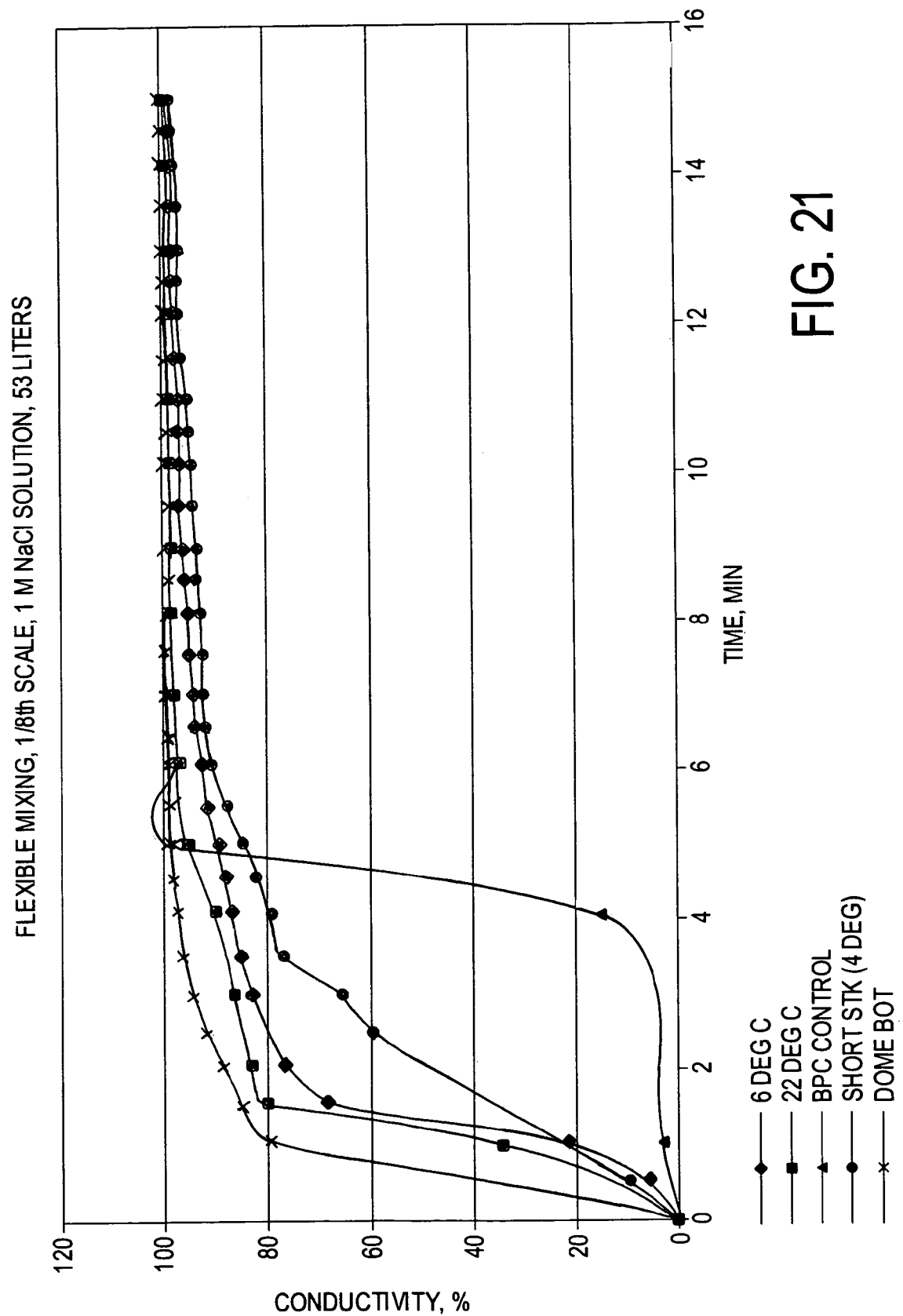
FIG. 21 is a graph which shows that the shape of the bottom of the vessel influences mixing speed.

Although the present invention has been described and illustrated in detail to a specific design and structure, such explanation is to be clearly understood that the same is by way of illustration and example only, and is not to be taken by way of limitation. Other modifications of the above examples may be made by those having ordinary skill in the art which remain within the scope of the invention. In the disclosure above, vessel 10 has been shown in this disclosure to be of a cylindrical shape, however, various other shapes and configurations are possible using the teachings of this invention. For example, rather than using a cylindrical-shaped vessel having, the vessel may have other shapes, such as those shown in FIGS. 15A through 15C, wherein a taper can be made in the side wall of the vessel to alter the effect of processes outlined above. The shape used should be chosen with the nature of the process required. In FIG. 15D there is shown a further modification of the vessel having a rectangular box design. Other three-dimensional designs are further possible, such as triangular boxes, hexagonal boxes, and other polygonal boxes and configurations. As shown in FIG. 21, the shape of the bottom of vessel 10 affects the speed of mixing, with a domed shape being preferable to a flat or dish-shaped bottom. Additionally, static mixers may be placed in perforations 400 to increase the degree of mixing.

Figure 15E:
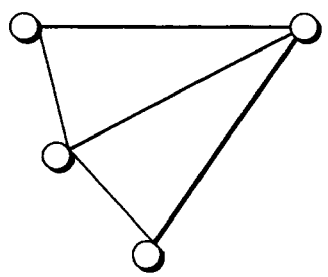
Figure 15F:
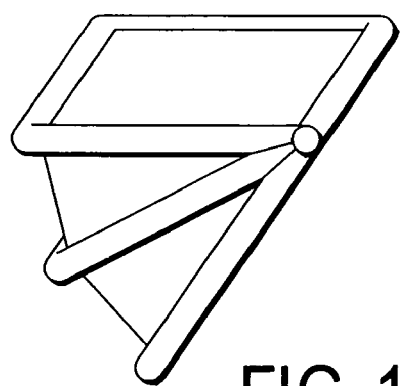

Further, the vessel need not necessarily have an accordion type of structure, which is shown and described herein, it may rather be more of a pivoting structure, as is shown in FIGS. 15E and 15F. In such a structure, upper disk, lower disk and septum are all pivoted about a pivot axis.

The vessel 10 may alternatively have rigid sides, and the fluid inside the vessel passes through the septum 500 by moving either the septum 500 or the ends of the container. In the embodiment shown in FIG. 24, vessel 10 is provided with one or more pistons 4000, disposed at opposite ends of the vessel. Typically, pistons 4000 are actuated by rods 4010, which cause any fluid or plastic disposed in the container to be forced through septum 500. Preferably, septum 500 is fixedly mounted to the sides of vessel 10, such that when piston 4000 pushes the fluid toward septum 500, the fluid is forced through septum 500. In one embodiment, vessel 10 is provided with a first piston 4000 at one end, and a second piston 4000' at the opposite end, such that when one piston 4000 moves inward, the force against the fluid pushes the second piston outward. Similarly, it is possible to push the first piston 4000 to create a positive force to push the fluid through septum, while simultaneously (or alternatively) pulling on the second piston 4000 to create a negative force, or vacuum, to pull the fluid through the septum 500. In order to eliminate fluid from leaking around the surface of the pistons 4000, each of the pistons are preferably provided with one or more seals 4020, e.g., an O-ring, lip seal or ring seal, between the pistons 4000 and the interior walls of the vessel 10. The seals are preferably formed from a resilient material, such as a natural or synthetic rubber, or other polymeric material, such as a polyolefin or metal, such as a spring seal or composites. The presence of seals 4020 allows for simple charging/discharging of the vessel 10, as one or both pistons can be easily removed.

Figure 24:
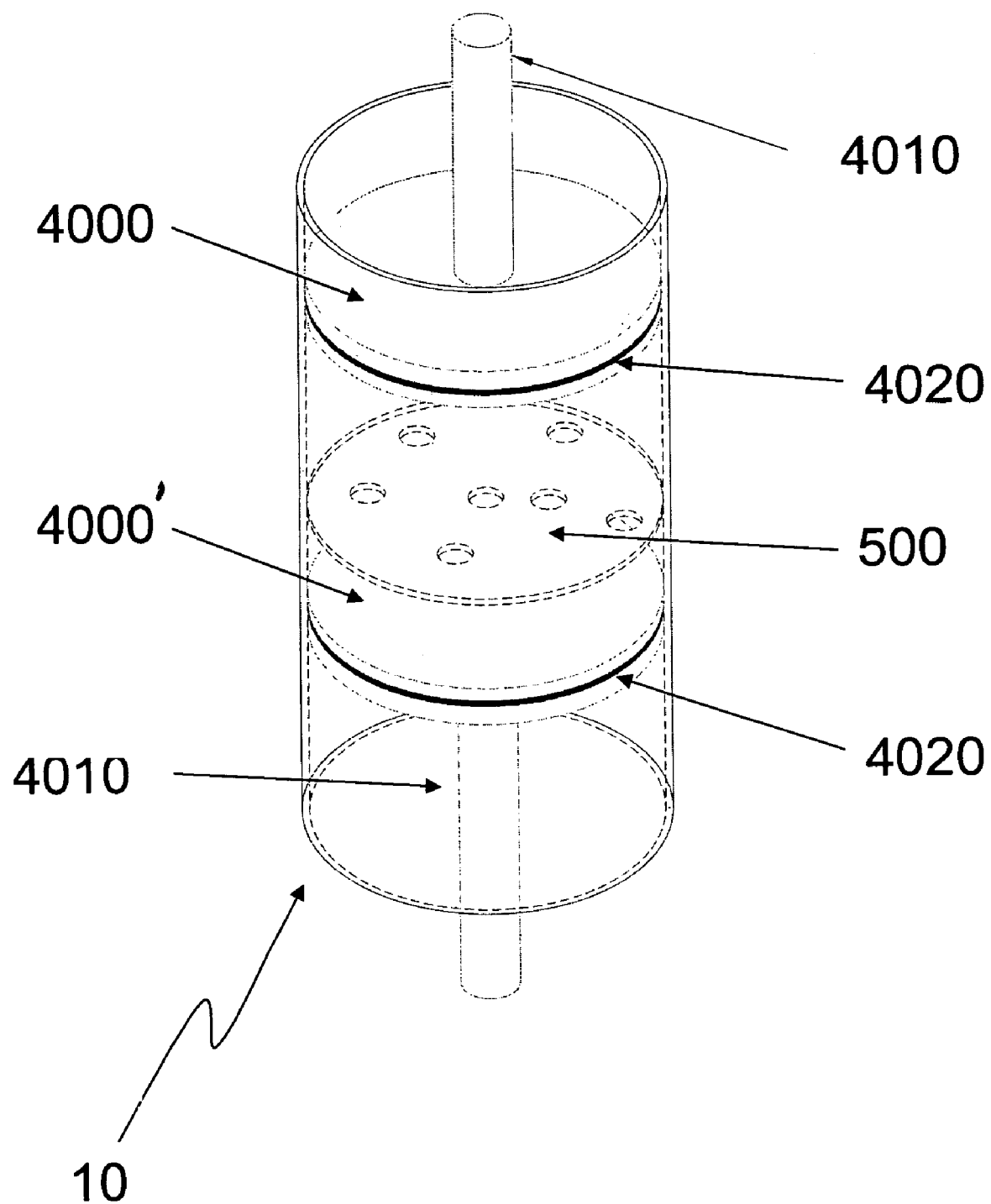
FIG. 24 shows an alternate embodiment wherein the septum is relatively moveable with respect to the container.

Although FIG. 24 shows the ends of the vessel 10 being movable and septum 500 being stationary, it is considered within the scope of the invention to employ any relative movement between the septum and pistons, e.g., to have septum 500 moveable and the ends of the vessel being stationary, e.g., with a single piston extending from one end of the vessel 10 to the septum 500. Each embodiment has the same overall effect, i.e., the ends of the vessel 10 shift with respect to the septum 500 in order to force fluid therethrough.

According to FIG. 24, each of the pistons 4000 are manually or mechanically actuated from outside the vessel 10. Alternatively, it is considered with in the scope of the invention to provide the actuating means inside the vessel 10, such that no external activation is necessary. If the force driving the pistons is hydraulic or pneumatic, a fluid pumping means can be disposed inside or outside vessel 10. If the pistons are electric, only cabling need pass through the walls of the vessel 10, requiring very little sealing. Additionally, the pistons 4000 can be actuated by a magnetic field, e.g., having one or magnets of a particular polarity disposed thereon, and generating a dynamic magnetic field by, for example, electrically or by moving one or magnets, of different polarities, adjacent the vessel 10 to create a dynamic or moving magnetic field.

Upon completion of mixing, one of the pistons 4000 can be removed, while the opposite piston 4000 is cycled to contact the septum 500, thereby pushing the entire volume of mixed medium to one side of the septum 500 for removal. Removal can be achieved by dumping or by vacuum extraction from above or below or alternatively through a side port.

Additionally, any or all of the steps/features/components of FIGS. 1-23 can be performed and/or combined with the apparatus of FIG. 24.

It should be apparent from this description that embodiments other than those described above come within the spirit and scope of the present invention. Finally, due to the construction, the vessels can be re-used, if only for limited times. Additionally, although the above-description has been made using a liquid, any fluid or combination of fluids may be used in either chamber.

We claim:

1. A vessel comprising a septum spaced intermediate a first and second opposite ends, said septum being attached to at least one wall of said vessel so as to divide the vessel into at least two chambers and having an open area expressed as percentage of the surface, between 10 to 90%, wherein at least one of said first and second ends comprises a piston, said piston arranged to moved said first or second chambers.

2. The vessel of claim 1, wherein said vessel comprises at least one port for introducing or removing components.

3. The vessel of claim 1, wherein said septum is relatively moveable with respect to said first and second ends.

4. The vessel of claim 1, wherein the septum comprises at least one element selected from the group consisting of micropores, a vacuum device, and moveable tubes embedded therein.

5. The vessel of claim 1, wherein each of said first and second ends comprise a piston.

6. The vessel of claim 1, wherein the septum is formed from at least one material selected from the group consisting of fabric, metal, plastic and ceramic.

7. The vessel of claim 1, wherein the septum is rigid.

8. The vessel of claim 1, wherein said septum has an open area, as a percentage of total area of said septum, between approximately 30 and approximately 75%.

9. A device comprising the vessel of claim 1, wherein the vessel is cylindrical.

10. A vessel comprising a septum spaced intermediate first and second opposite ends, said septum being attached to at least one wall of said vessel so as to divide the vessel into at least two chambers, wherein at least one of said first and second ends comprises a piston, further comprising at least one perfusion filter positioned at least one of the chambers in said vessel.

11. A method comprising:
repeatedly relatively passing a fluid from a first chamber to a second chamber in a vessel, including passing said fluid through a septum by moving said septum with respect to ends of said first and second chambers, by a piston provided at least at one end of the vessel and moving an end of at least one of said first and second chambers.

12. The method of claim 11, further comprising removing gas from at least one of the first chamber and the second chamber.

13. The method of claim 11, further comprising introducing an inert atmosphere to at least one of the first chamber and the second chamber.

14. The method of claim 11, wherein said method is at least one selected from the group consisting of mixing, reacting, fermenting, filtering, sterilizing, lysing and ion exchanging.

15. The method of claim 11, wherein said passing comprises moving the septum through the fluid.

16. The method of claim 11, wherein said passing comprises moving at least one piston to provide pressure to said fluid.

17. The method of claim 16, wherein said pressure is a negative pressure.

18. The method of claim 16, wherein said passing comprises moving two pistons to provide pressure to said fluid.

19. A method comprising:
repeatedly relatively passing a fluid from a first chamber to a second chamber in a vessel, including passing said fluid through a septum by moving said septum with respect to ends of said first and second chambers said septum is attached to at least one wall of the vessel, the method further comprising at least one step of heating and cooling the fluid in the vessel.

20. The method of claim 19, wherein said heating or cooling comprises passing a heating or cooling fluid through the septum.

21. A method comprising:
providing a vessel having a first and a second chambers divided by a septum attached to at least one wall of the vessel; introducing a fluid into the vessel; repeatedly relatively passing the fluid through the septum by moving the septum with respect to the end of said first and second chambers, and further introducing a second component into the vessel.

22. The method of claim 21 wherein the second component is a pigment.

\* \* \* \* \*